United States Patent
Bowser et al.

(10) Patent No.: US 12,050,217 B2
(45) Date of Patent: Jul. 30, 2024

(54) CHITINASE PROTEINS IN NEUROLOGIC DISEASE

(71) Applicant: Dignity Health, San Francisco, CA (US)

(72) Inventors: Robert Bowser, San Francisco, CA (US); Lucas Vu, San Francisco, CA (US)

(73) Assignee: Dignity Health, Sanfrancisco, CA (US)

( * ) Notice: Subject to any disclaimer, the term of this patent is extended or adjusted under 35 U.S.C. 154(b) by 0 days.

(21) Appl. No.: 17/157,387

(22) Filed: Jan. 25, 2021

(65) Prior Publication Data

US 2021/0231660 A1     Jul. 29, 2021

Related U.S. Application Data

(60) Provisional application No. 62/965,528, filed on Jan. 24, 2020.

(51) Int. Cl.
G01N 33/573     (2006.01)

(52) U.S. Cl.
CPC .... *G01N 33/573* (2013.01); *C12Y 302/01014* (2013.01); *G01N 2496/00* (2013.01); *G01N 2800/52* (2013.01)

(58) Field of Classification Search
CPC ............. G01N 33/573; G01N 2496/00; G01N 2800/52; G01N 33/6896; C12Y 302/01014
See application file for complete search history.

(56) References Cited

U.S. PATENT DOCUMENTS

2017/0157197 A1    6/2017    Ko et al.

OTHER PUBLICATIONS

Franc Llorens (YKL-40 in the brain and cerebrospinal fluid of neurodegenerative dementias Molecular Neurodegeneration (2017) 12:83, p. 1-21) (Year: 2017).*
Thompson AG, et al. CSF chitinase proteins in amyotrophic lateral sclerosis. J Neurol Neurosurg Psychiatry 2019;90:1215-1220 (Year: 2019).*
Of Rakesh Aggarwal et al. Understanding diagnostic tests—Part 3: Receiver operating characteristic curves Rakesh Aggarwal et al Perspectives in Clinical Research Statistics, p. 145-148. vol. 9 | Issue 3 | Jul.-Sep. 2018. (Year: 2018).*
Patent Cooperation Treaty, International Search Report and Written Opinion, International Application No. PCT/US2019/019671, date of mailing May 6, 2019, 12 pages.
Varghese, A. M., et al., "Chitotriosidase—a putative biomarker for sporadic amyotrophic lateral scherosis," Clinical Protemomics, vol. 10, 2013, pp. 1-9.
Di Rosa, M. et al. "Evaluation of CHI3L-1 and CHIT-1 Expression in Differentiated and Polarized Macrophages," Inflammation, vol. 36, No. 2, Nov. 14, 2012, pp. 482-492.
Thompson, A. G. et al., "Cerebrospinal Fluid Macrophage Biomarkers in Amyotrophic Lateral Sclerosis," Annals of Neurology, vol. 83, No. 2, Jan. 9, 2018, pp. 258-268, p. 261.

* cited by examiner

*Primary Examiner* — Soren Harward
*Assistant Examiner* — Robert James Kallal
(74) *Attorney, Agent, or Firm* — Polsinelli PC

(57) ABSTRACT

The present disclosure describes methods of determining a treatment protocol for and/or a prognosis for a subject suspected of or at risk of suffering from a neurologic disease or disorder, including such diseases and disorders that involve motor neuron function such as ALS. The methods comprise detecting the presence of a chitinase protein in a biological sample.

3 Claims, 41 Drawing Sheets

CHITINASE PROTEINS IN NEUROLOGIC DISEASE

CROSS-REFERENCE TO RELATED APPLICATIONS

This application claims priority from Provisional Application No. 62/965,528, filed Jan. 24, 2020, the contents of which is hereby incorporated by reference in its entirety.

FIELD OF THE INVENTION

The present disclosure generally relates to methods of determining a treatment protocol and/or a prognosis for a subject suspected of or at risk of suffering from a neurologic disease or disorder.

BACKGROUND OF THE INVENTION

Inflammation in the peripheral nervous system and central nervous system is a key element of many serious neurologic diseases for which diagnostic, prognostic, and monitoring methods are generally lacking. Further, such diseases can be difficult to discriminate among the others that share clinical signs. For example, early detection and diagnosis of Amyotrophic lateral sclerosis (ALS) is difficult because its signs can be very similar to other neurologic diseases. Methods for diagnosing ALS currently include Electromyogram (EMG), nerve conduction study, magnetic resonance imaging (MRI), spinal tap (lumbar puncture), or muscle biopsy, but many of these tests only function to rule out other possibilities. A need remains for a test capable of discriminating among neurologic diseases that share clinical signs.

SUMMARY OF THE INVENTION

One aspect of the present disclosure encompasses a method of determining an optimal cutoff chitinase concentration for categorizing a subject as having a neurological disease or disorder. The method comprises obtaining or having obtained chitinase protein concentrations measured in samples obtained from subjects having the neurological disease or disorder and biological samples from control subjects. The method further comprises obtaining a receiver (ROC) curve by applying a statistical modeling technique using the chitinase protein concentrations, and calculating a Youden index for each point of the ROC curve. The highest calculated Youden index represents the optimal cutoff concentration, and the optimal cutoff concentration distinguishes subjects having a neurological disease or disorder.

The chitinase protein concentrations can be measured using an immunoassay. In some aspects, the chitinase protein is Chit-1, CHI3L1, or combinations thereof. The neurological disease can be amyotrophic lateral sclerosis (ALS), and the optimal cutoff concentration can distinguish subjects having fast progressing ALS, slow progressing ALS, and healthy subjects.

Another aspect of the present disclosure encompasses a method of categorizing a human subject for treatment. The subject is suspected of having or being at risk of having a neurologic disease or disorder. The method comprises performing an immunoassay to determine a concentration of one or more chitinase proteins in a biological fluid sample obtained from the subject. The method further comprises comparing the concentration of the one or more chitinase proteins in a biological fluid sample to an optimal cutoff concentration of the chitinase derived from suitable controls. A concentration of the chitinase proteins in the biological sample equal to or higher than the optimal cutoff concentration of the chitinase is indicative of neurologic disease or disorder in the subject and the subject is confirmed as a candidate for a neurologic treatment. The optimal cutoff concentration can be determined as described above.

The biological sample can be cerebrospinal fluid (CSF) and the chitinase protein can be Chit-1. When the biological sample is CSF, the chitinase protein is Chit-1, and the neurological disease is ALS, the optimal cutoff concentration for Chit-1 can be about 6.24 ng/ml in the CSF.

In some aspects, the chitinase protein is CHI3L1 and the neurological disease or disorder is selected from the group consisting of ALS, Alzheimer's disease, Parkinson's disease, frontotemporal dementia, brain metastases, viral encephalitis, neuropathy, multiple sclerosis, upper motor neuron disease, primary lateral sclerosis, chronic inflammatory demyelinating polyneuropathy, idiopathic sensorimotor polyneuropathy, spinocerebellar ataxia, lymphoma, and lower motor neuron disease. When the biological sample is CSF, the chitinase protein is CHI3L1, and the neurological disease is selected from the group consisting of ALS, Alzheimer's disease, Parkinson's disease, frontotemporal dementia, brain metastases, viral encephalitis, neuropathy, multiple sclerosis, upper motor neuron disease, primary lateral sclerosis, chronic inflammatory demyelinating polyneuropathy, idiopathic sensorimotor polyneuropathy, spinocerebellar ataxia, lymphoma, and lower motor neuron disease, the optimal cutoff concentration for Chit-1 can be about 281.3 ng/ml in the CSF biological sample.

Yet another aspect of the present disclosure encompasses a method of monitoring the therapeutic effect of an ALS treatment protocol in a subject being treated with the ALS treatment protocol. The method comprises performing an immunoassay to determine a concentration of Chit-1 in a first biological sample obtained from the subject, and in a second biological fluid sample obtained from the subject at a period of time after the first biological sample is obtained. The method further comprises comparing the concentration of Chit-1 in the first and second biological fluid samples, wherein a decreased or maintained concentration of Chit-1 in the second sample relative to the first sample is indicative that the treatment protocol is therapeutically effective in the subject.

DETAILED DESCRIPTION

Figure 1A:
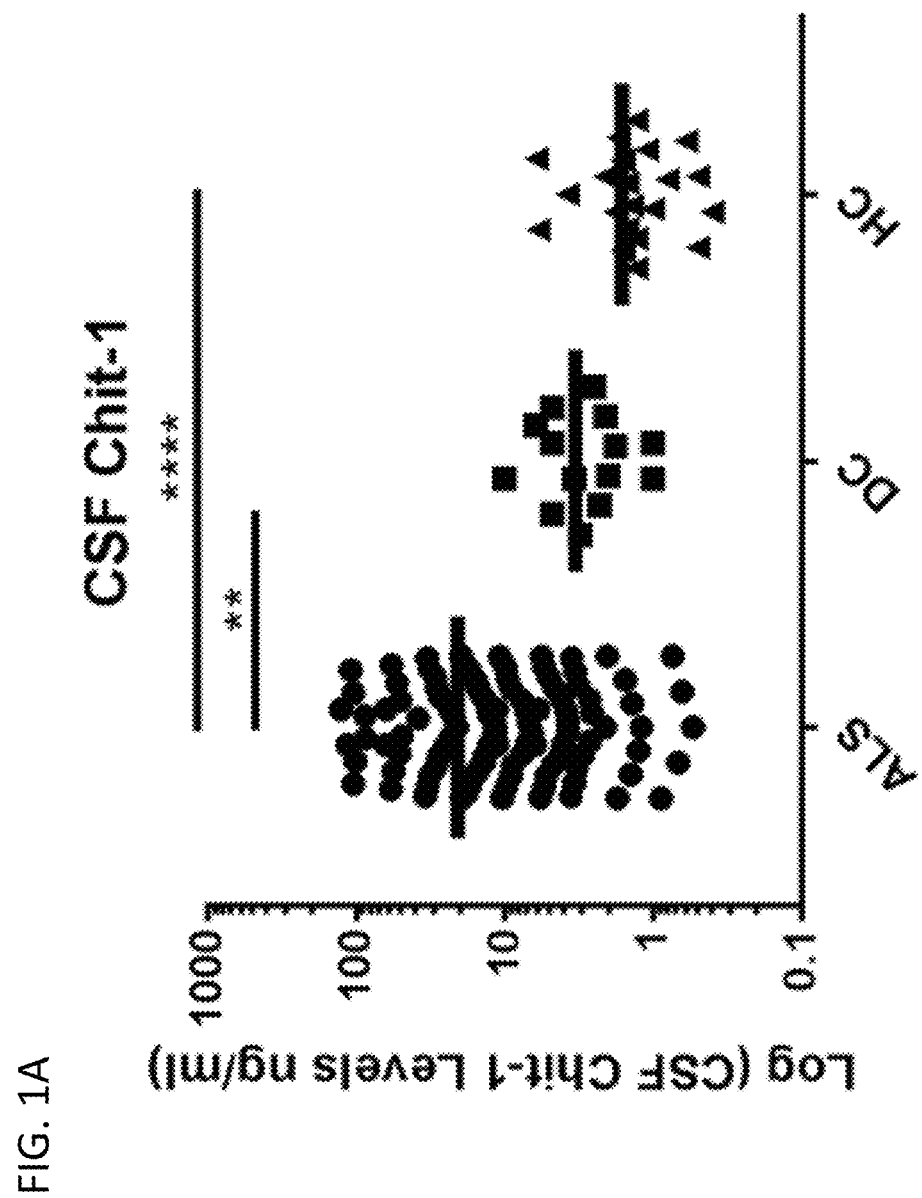
FIG. 1A. Concentration of CSF Chit-1 using data from baseline visits for ALS patients, disease controls (DC), and healthy controls (HC). *$p<0.05$, $p<0.01$, *$p<0.001$, ****$p<0.0001$, and NS=not significant.

The inventors developed statistical methods and histological methods that can be used to categorize a subject as having a neurological disease or disorder. The methods disclosed herein are useful for diagnosis and prognosis, for clinical trials to stratify patient populations, to provide a personalized treatment protocol, phenotype for selection to participate in drug trials, predict the rate of progression of a neurological disease or disorder in the subject, and to monitor efficacy of therapies that target specific neurological diseases and disorders. Importantly, the methods are capable of diagnosing a subject with high accuracy and specificity.

I. Methods

One aspect of the present disclosure provides methods of determining an optimal cutoff chitinase concentration for categorizing a subject as having a neurological disease or disorder, and methods of using the optimal cutoff chitinase concentration to diagnose and prognose neurological disorders, for clinical trials to stratify patient populations, to provide a personalized treatment protocol, phenotype for selection to participate in drug trials, predict the rate of progression of a neurological disease or disorder in the subject, and to monitor efficacy of therapies that target specific neurological diseases and disorders.

(a) Subject

The subject can be, without limitation, a human, a non-human primate, a mouse, a rat, a guinea pig, or a dog. In some aspects, the subject is a human subject. The subject can be suspected of having or is at risk of having a neurologic disease or disorder. Non-limiting examples of a neurological disease or condition include ALS, Alzheimer's disease, Parkinson's disease, frontotemporal dementia, brain metastases, viral encephalitis, neuropathy, multiple sclerosis, upper motor neuron disease, primary lateral sclerosis, chronic inflammatory demyelinating polyneuropathy, idiopathic sensorimotor polyneuropathy, spinocerebellar ataxia, lymphoma, Bell's palsy, epilepsy, and lower motor neuron disease.

When the subject has ALS, the methods of the instant disclosure can be used to stratify subjects into fast progressors (FPs), slow progressors (SPs) and intermediate progressors (IPs) using the disease progression rate. Disease progression rate can be defined by the change in ALS functional rating scale revised (ALSFRS-r) between the last and baseline visits/the amount of months between the visits. Fast progressors (FPs) can be defined as those having a disease progression rate 1 unit/month, slow progressors (SPs) as subjects having a disease progression rate <0.5 units/month, and intermediate progressors (IPs) as subjects having a disease progression rate 0.5 units/month but less than 1 unit/month.

(b) Chitinases

The methods comprise detecting the presence or measuring the concentration of one or more chitinases in a sample obtained from the subject. Chitinases and chitinase-like proteins, collectively referred to as chitinase proteins or chitinases, are members of the glycoside hydrolase family 18 and function to degrade chitin, modulate innate immune responses, cell migration and differentiation, and modulate inflammation in the progression of many human diseases. To date, six chitinase or chitinase-like proteins have been identified in humans: SI-CLP (CHID1), YKL-39 (CHI3L2), YKL-40 (CHI3L1), Chitriosidase (Chit-1), AMCase (CHIA), and oviductin. Chitotriosidase (Chit-1) was the first identified mammalian chitinase protein that both binds and degrades chitin. Other members of the chitinase family, such as chitinase-3-like protein 1 (CHI3L1) or chitinase-3-like protein 2 (CHI3L2), bind chitin but do not exhibit enzymatic activity. Additional chitinase proteins such as YM1 and YM2 (Chi3l3/14) have been identified in certain non-human mammals. Accordingly, the concentration or the presence of SI-CLP, YKL-39 (CHI3L2), YKL-40 (CHI3L1), Chitriosidase (Chit-1), AMCase, oviductin, YM1, YM2, or combinations thereof can be determined in methods of the instant disclosure. In some aspects, the chitinase protein is CHI3L1, Chit-1, or combinations thereof.

(c) Immunoassay

In some aspects, the methods of the instant disclosure comprise measuring the concentration of one or more chitinases in a biological sample obtained from the subject. Accordingly, aspects of the instant disclosure further comprise a method of analyzing a biological sample obtained from a subject.

A biological sample may include, but is not limited to, a cell, a cellular organelle, an organ, a tissue, a tissue extract, a biofluid, or an entire organism. The sample may be a heterogeneous or homogeneous population of cells or tissues. As such, chitinase levels or concentrations can be measured within cells, tissues, organs, or other biological samples obtained from the subject. For instance, the biological sample can be bone marrow extract, whole blood, blood plasma, serum, peripheral blood, urine, phlegm, synovial fluid, milk, saliva, mucus, sputum, exudates, cerebrospinal fluid, intestinal fluid, tissue digests, tumor cell containing cell suspensions, cell suspensions, and cell culture fluid which may or may not contain additional substances (e.g., anticoagulants to prevent clotting). The sample can comprise cells or can be cell free. In some aspects, the sample is cerebrospinal fluid. In another aspect, the sample is a plasma sample. In other aspects, the sample is neuronal tissue.

In some aspects, multiple biological samples may be obtained for diagnosis by the methods of the present invention, e.g., at the same or different times. A sample or samples obtained at the same or different times can be stored and/or analyzed by different methods.

Methods for obtaining and extracting a protein such as a chitinase from a wide range of biological samples, including cell cultures, urine, blood/serum, and both animal- and plant-derived tissues are known in the art. Although these protocols are readily available, the variable stability of metabolites and the source of a sample means that even minor changes in procedure can have a major impact on the observed metabolome. For instance, the fast turnover rate of enzymes and the variable temperature and chemical stability of metabolites require that metabolomics samples be collected quickly and handled uniformly, and that all enzymatic activity be rapidly quenched in order to minimize biologically irrelevant deviations between samples that may result from the processing protocol.

The method further comprises performing an immunoassay to measure the concentration of, or determine the presence of one or more chitinase proteins in each biological sample. In some aspects, the presence or absence of a chitinase in cells of a tissue sample is determined. Determining the presence of a protein in a biological tissue sample can be by immunohistochemistry using methods known in the art. In some aspects, the method comprises performing an immunohistochemical assay to detect the presence of a chitinase protein in a specific cell type in a tissue sample obtained from the central nervous system of the subject. In some aspects, the sample obtained from the central nervous system comprises grey matter and white matter.

In some aspects, the concentration of one or more chitinase proteins is measured in a biological sample. Methods of measuring the concentration of a protein such as a chitinase protein in a sample are known in the art, and can and will vary depending on the protein, the number of proteins to be measured, and the biological sample in which the proteins are measured, among other variables, and can be determined experimentally. There are numerous known immunoassay methods and kits for measuring the amount or concentration of a specific protein in a complex sample, including enzyme linked immunosorbant assay (ELISA), western blot, or other solid phase immunoassays, radioimmunoassay, nephelometry, electrophoresis, immunofluorescence, immunoblot, or other methods (see Ausubel, F. M. et al., eds., Current Protocols in Molecular Biology, John Wiley & Sons, including supplements through 2001). Determining the presence of a protein in a biological tissue sample can be by immunohistochemistry using methods known in the art.

In some aspects, the immunoassay is an ELISA. ELISA is a plate-based assay technique designed for detecting and quantifying substances such as peptides, proteins, antibodies, and hormones. Other names, such as enzyme immunoassay (EIA), are also used to describe the same technology. In an ELISA, an antigen is immobilized on a solid surface and then complexed with an antibody that is linked to a detection enzyme. Detection is accomplished by assessing the conjugated enzyme activity via incubation with a substrate to produce a measureable product. The most crucial element of the detection strategy is a highly specific antibody-antigen interaction.

A detection enzyme or other tag can be linked directly to a primary antibody or introduced through a secondary antibody that recognizes the primary antibody. A detection enzyme can also be linked to a protein such as streptavidin if the primary antibody is biotin labeled. Non-limiting examples of enzyme labels are horseradish peroxidase (HRP), alkaline phosphatase (AP), β-galactosidase, acetylcholinesterase, and catalase. A large selection of substrates is available for performing ELISA with an HRP or AP conjugate. The choice of substrate depends upon the required assay sensitivity and the instrumentation available for signal-detection (spectrophotometer, fluorometer or luminometer), and may be determined experimentally.

ELISAs can be performed using a number of formats. Immobilization of the antigen of interest can be accomplished by direct adsorption to the assay plate or indirectly via a capture antibody that has been attached to the plate. The antigen is then detected either directly (labeled primary antibody) or indirectly (labeled secondary antibody). A direct detection method uses a labeled primary antibody that reacts directly with the antigen. Direct detection can be performed with an antigen that is directly immobilized on the assay plate or with the capture assay format. An indirect detection method uses a labeled secondary antibody for detection. The secondary antibody has specificity for the primary antibody.

Generally, the immunoassay methods employed herein have relatively low limits of detection or of quantification as compared to commercially available ELISA kits. A well-known and highly specific ELISA is a sandwich ELISA in which the antibody is bound to a solid phase or support, which is then contacted with the sample being tested to extract the antigen from the sample by formation of a binary solid phase antibody:antigen complex. In a sandwich ELISA, the secondary antibody is generally specific for the detection primary antibody only (and not the capture antibody). Generally, this is achieved by using capture and primary antibodies from different host species (e.g., mouse IgG and rabbit IgG, respectively). After a suitable incubation period, the solid support is washed to remove the residue of the fluid sample and then contacted with a solution containing a known quantity of labeled antibody. ELISA assays measure the amount of target protein (analyte) in a biological fluid sample. Basic ELISA methods and materials such as ELISA plates and capture and detection antibodies for performing ELISA assays of specific target analytes in fluid samples, are well known and readily commercially available.

An ELISA assay may be optimized. ELISA optimization may include systematically adjusting and testing components and variables of the assay to help ensure results are robust and accurate. For instance, optimization may comprise identifying preferred components of an ELISA, such as blocking buffer, wash buffer, detection antibody, enzyme conjugate, signal detection, and other buffers and diluents and concentrations thereof.

The terms "limit of detection" ("LOD") and "limit of quantification" ("LOQ") adhere to their ordinary meaning in the art. LOD refers to the lowest analyte concentration likely to be reliably distinguished from background noise and at which detection is feasible, and as used herein is a signal which is three standard deviations (SD) above background noise. LOQ refers to the lowest concentration at which the analyte is reliably detected and meets predefined goals for bias and imprecision. Generally, as used herein, LOQ refers to the lowest concentration above the LOD wherein the coefficient of variation (CV) of the measured concentrations is less than about 20%.

The concentration of analyte (target) molecules in a fluid sample may be considered to be substantially accurately determined if the measured concentration of the target molecules in the fluid sample is within about 10% of the actual concentration of the molecules in the fluid sample. In certain aspects, the measured concentration of the target molecules in the fluid sample may be within about 5%, within about 4%, within about 3%, within about 2%, within about 1%, within about 0.5%, within about 0.4%, within about 0.3%, within about 0.2%. or within about 0.1% of the actual concentration of the biomarker molecules in the fluid sample. In some cases, the measured concentration differs from the actual concentration by no greater than about 20%, no greater than about 15%, no greater than 10%, no greater than 5%, no greater than 4%, no greater than 3%, no greater than 2%, no greater than 1%, or no greater than 0.5%. The accuracy of the assay method may be determined, in some aspects, by determining the concentration of target molecules in a fluid sample of a known concentration using the selected assay method.

(d) Determining Optimal Cutoff Concentrations

One aspect of the present disclosure encompasses a method of determining an optimal cutoff concentration for categorizing a subject as having a neurological disease or disorder. The method comprises performing statistical analysis to determine the optimal cutoff concentration of a chitinase in a sample. As defined herein, an optimal cutoff concentration of a chitinase refers to a concentration of a chitinase protein in a biological sample obtained from a subject at or above which a subject can be confirmed as having a neurological disease. In other words, when the concentration of a chitinase in a sample obtained from a subject is equal to or higher than a cutoff concentration of the chitinase, the subject is confirmed as having the neurological disease. Conversely, when the concentration of a chitinase in a sample obtained from a subject is lower than a cutoff concentration of the chitinase, the subject is confirmed as healthy or free of the neurological disease. Accordingly, the cutoff concentration of chitinase in a biological sample can stratify a subject as having a neurological condition if the concentration of the chitinase is equal to or above the cutoff concentration. When the neurological disease is ALS, the cutoff concentration of chitinase in a biological sample can further stratify a subject as having fast progressing ALS or slow progressing ALS if the concentration of the chitinase is equal to or above the cutoff concentration.

It will be recognized that the cutoff concentration can and will vary depending on the chitinase and the sample in which the chitinase is measured. For instance, a cutoff concentration of Chit-1 in CSF can be different from the cutoff concentration of CHI3L1 in CSF. Similarly, a cutoff concentration of Chit-1 in CSF can be different from the cutoff concentration of Chit-1 in plasma. As explained further below, the optimal cutoff concentration can be determined using statistical analysis of chitinase concentrations obtained from suitable control subjects. Suitable control subjects can include healthy subjects and subjects having the neurological disorder. When the neurological disease is ALS, control subjects can be fast progressors or slow progressors.

The statistical analysis comprises applying a binary statistical classification method capable of classifying elements of a set of measurements into two groups, with a cutoff value separating the two groups. Binary classification methods suitable for the instant disclosure are known in the art, and can determine an optimal cutoff that maximizes sensitivity and/or specificity to serve as a threshold for discriminating samples obtained from subjects with a neurological disorder. Non-limiting examples of binary classification methods include classification tree analysis, random forests, Bayesian networks, and LASSO (least absolute shrinkage and selection operator) logistic regression analysis.

In some aspects, an optimal cutoff concentration of the instant disclosure is determined by calculating a Youden index for each point of an ROC curve. Youden's index (also called Youden's J statistic) is a single statistic that captures the performance of a dichotomous diagnostic test. A Youden index maximizes the difference between the true positive and false positive rates. A Youden's index is calculated according to the following equation:

$$J=\text{sensitivity}+\text{specificity}-1$$

or, using the expanded equations that further show how sensitivity and specificity are calculated:

$$J = \frac{\text{true positives}}{\text{true positives} + \text{false negatives}} + \frac{\text{true negatives}}{\text{true negatives} + \text{false positives}} - 1$$

The index summarizes the performance of a diagnostic test. Its value ranges from 0 through 1 (inclusive). The index has a zero value when a diagnostic test gives the same proportion of positive results for groups with and without the disease. A value of 1 indicates that there are no false positives or false negatives.

Youden's index is often used in conjunction with receiver operating characteristic (ROC) analysis. The index is defined for all points of an ROC curve, and the maximum value of the index may be used as a criterion for selecting the optimum cutoff point when a diagnostic test gives a numeric rather than a dichotomous result. The index is represented graphically as the height above the chance line, and it is also equivalent to the area under the curve subtended by a single operating point.

In some aspects, a cutoff concentration is determined using ROC curve analysis. As used herein, the term "ROC" means "receiver operating characteristic." An ROC analysis may be used to evaluate the diagnostic performance or predictive ability of a test or a method of analysis. An ROC graph is a plot of sensitivity and specificity of a test at various thresholds or cutoff values. Each point on an ROC curve represents the sensitivity and its respective specificity. A threshold value can be selected based on an ROC curve, wherein the threshold value is a point where sensitivity and specificity both have acceptable values. The threshold value can be used in applying the test for diagnostic purposes. It will be understood that if only specificity is optimized, then the test will be less likely to generate a false positive (diagnosis of the disease in more subjects who do not have the disease) at the cost of an increased likelihood that some cases of disease will not be identified (e.g., false negatives). If only sensitivity is optimized, the test will be more likely to identify most or all of the subjects with the disease, but will also diagnose the disease in more subjects who do not have the disease (e.g., false positives). A user is able to select an ROC threshold value suitable for a given clinical situation, in ways that will be readily understood by those skilled in the art. Methods of selecting an ROC threshold include calculating a Youden index, calculating a maximum vertical distance MVD between the chance diagonal and the ROC curve, or the like.

Accordingly, in some aspects, methods of the instant disclosure comprise obtaining an ROC curve by applying a statistical modeling technique using the chitinase protein concentrations measured in samples obtained from suitable control subjects. In some aspects, a Youden index is calculated for each point of the ROC curve, and the highest calculated Youden index identifies the optimal cutoff concentration.

(e) Methods of Diagnosing

Methods of the instant disclosure can diagnose a subject with a neurological disease or disorder. The method can diagnose a neurologic disease with a surprisingly high level of sensitivity and specificity. For instance, the method can diagnose ALS in a subject with a sensitivity greater than or equal to 60%, greater than or equal to 70%, greater than or equal to 80%, greater than or equal to 90%, or even with a 100% sensitivity. The method can also diagnose ALS with a surprisingly high level of specificity. For instance, the method can diagnose ALS in a subject with a specificity greater than or equal to 90%, greater than or equal to 91%, greater than or equal to 92%, greater than or equal to 93%, greater than or equal to 94%, greater than or equal to 95%, greater than or equal to 96%, greater than or equal to 97%, greater than or equal to 98%, greater than or equal to 99%, or even with a 100% specificity. In some aspects, the method can diagnose ALS with a sensitivity of at least about 60% to about 90%, a specificity of at least about 80% to 90%, or both.

Some aspects of the present disclosure provide a method of categorizing for treatment a subject suspected of having or at risk of having a neurologic disease or disorder. The method comprises determining the concentration of one or more chitinase proteins in a biological fluid sample obtained from the subject. Determining the concentration of one or more chitinase proteins can be as described in Section I(c). In some aspects, the concentration of the one or more chitinase proteins is determined by performing an immunoassay. In some aspects, the immunoassay is an ELISA assay. Immunoassays and ELISA assays can be as described in Section I(c).

The method further comprises comparing the concentration of the one or more chitinase proteins in a biological fluid sample to an optimal cutoff concentration of the chitinase derived from suitable controls. A concentration of the chitinase protein in the biological fluid sample equal to or higher than the optimal cutoff concentration of the chitinase is indicative of neurologic disease or disorder in the subject, and the subject is confirmed as a candidate for a neurologic treatment. The optimal cutoff concentration can be as described in Section I(d).

The methods disclosed herein provide the ability to discriminate ALS sufferers from individuals suffering from other neurologic diseases that share clinical signs with ALS. For instance, when the concentration of CHI3L1 in CSF obtained from a subject is equal to the cutoff concentration, the subject is diagnosed as having a neurological disease or disorder. When the concentration of Chit-1 in CSF obtained from a subject is equal to the Chit-1 cutoff concentration, the subject is diagnosed as having ALS. Neurologic diseases or disorders that share clinical signs with ALS can include Alzheimer's disease, Parkinson's disease, frontotemporal dementia, brain metastases, viral encephalitis, neuropathy, multiple sclerosis, upper motor neuron disease, primary lateral sclerosis, chronic inflammatory demyelinating polyneuropathy, idiopathic sensorimotor polyneuropathy, spinocerebellar ataxia, lymphoma, or lower motor neuron disease.

In some aspects, the biological sample is CSF. When the chitinase protein is CHI3L1, the optimal cutoff concentration of CHI3L1 in the CSF can range from about 260 ng/ml to about 300 ng/ml, from about 270 ng/ml to about 290 ng/ml, from about 275 ng/ml to about 285 ng/ml. In some aspects, the optimal cutoff concentration of CHI3L1 in the CSF is about 281.3 ng/mL in the CSF biological sample. When the chitinase protein is CHI3L1, the optimal cutoff concentration of Chit-1 in the CSF ranges from about 4 ng/ml to about 9 ng/ml, from about 5 ng/ml to about 8 ng/ml, or from about 6 ng/ml to about 87 ng/ml. In some aspects, the optimal cutoff concentration of Chit-1 in the CSF is about 6.24 ng/ml in the CSF biological sample.

Yet another aspect of the present disclosure provides a method of categorizing for treatment a subject having a neurological disease or disorder. The method comprises determining the concentrations of Chit-1 and CHI3L1 proteins in a biological fluid sample obtained from the subject. Determining the concentration of chitinase proteins can be as described in Section I(c). In some aspects, the concentrations of Chit-1 and CHI3L1 are determined by performing an immunoassay. In some aspects, the immunoassay is an ELISA assay.

The method further comprises comparing the concentration of Chit-1 to an optimal cutoff concentration of Chit-1, and comparing the concentration of CHI3L1 to an optimal cutoff concentration of CHI3L1. The optimal cutoff concentration of Chit-1 and the optimal cutoff concentration of CHI3L1 are derived from suitable controls as described in Section I(d) above. A concentration of the CHI3L1 in the biological fluid sample equal to or higher than the optimal cutoff concentration of CHI3L1 is indicative of neurologic disease or disorder in the subject, and the subject is confirmed as a candidate for a neurologic treatment, and a concentration of Chit-1 in the biological fluid sample equal to or higher than the optimal cutoff concentration of Chit-1 is indicative of ALS in the subject, and the subject is confirmed as a candidate for ALS.

An additional aspect of the present disclosure provides a method of determining a treatment protocol for a subject suspected of having or at risk of having a neurological disease or disorder. The method comprises performing an immunoassay to determine a concentration of one or more chitinase proteins in a biological fluid sample obtained from the subject. The method further comprises comparing the concentration of the one or more chitinase proteins in a biological fluid sample to an optimal cutoff concentration of the chitinase derived from suitable controls. A treatment protocol is assigned to the subject if a concentration of the chitinase protein in the biological fluid sample is equal to or higher than the optimal cutoff concentration of the chitinase. In some aspects, the chitinase protein is Chit-1 and the neurological disease or disorder is ALS.

As noted above, different human chitinases are highly expressed in various inflammatory conditions and diseases, and in particular those impacting motor neurons. For example, neuroinflammation is a common characteristic of human subjects with ALS, manifesting as microglial activation, astrogliosis, and infiltration of monocytes and T-cells. Very early stage ALS is believed to involve the release of signals from motor neurons to microglia to release neuroprotective factors, proceeding to an imbalance leading to the disease phenotype. Thus it is believed that candidate therapies involving anti-inflammatory action may benefit subjects suffering from ALS. For example, candidate anti-inflammatory compounds that have recently been investigated for treating ALS include celecoxib, erythropoietin, glatiramer acetate, minocycline, NP001, pioglitazone, and valproic acid. That these candidates have not been successful in treating ALS to date does not preclude successful candidate anti-inflammatory compounds being identified in the near future. Identifying subjects for which candidate anti-inflammatory compounds may be beneficial is thus one application of the methods disclosed herein. The methods disclosed herein provide the ability to identify early stage ALS sufferers at a relatively low cost, and can be employed painlessly to stratify the subject into slow- or moderate-progressing or fast-progressing categories. With a positive immunoassay result, a subject at a very early stage of disease may be beneficially assigned to an anti-inflammatory treatment protocol to slow progress of the disease.

One aspect of the present disclosure provides a method of monitoring the therapeutic effect of an ALS treatment protocol in a subject being treated with the ALS treatment protocol. The method comprises performing an immunoassay to determine a concentration of Chit-1 in a first biological sample obtained from the subject, and in a second biological fluid sample obtained from the subject at a period of time after the first biological sample is obtained. The method further comprises comparing the concentration of Chit-1 in the first and second biological fluid samples, wherein a decreased or maintained concentration of Chit-1 in the second sample relative to the first sample is indicative that the treatment protocol is therapeutically effective in the subject.

One aspect of the present disclosure encompasses methods of categorizing for treatment a subject suspected of having or at risk of having a neurologic disease or disorder. The method comprises performing an assay to detect CHI3L1 in a specific cell type in a tissue sample obtained from the central nervous system of the subject. The sample obtained from the central nervous system comprises grey matter and white matter. Detection of CHI3L1 in astrocytes of the white matter, absence of CHI3L1 in microglia of the white matter, and absence of CHI3L1 in cells of the grey matter is indicative of ALS in the subject and the subject is confirmed as a candidate for ALS treatment. In some aspects the method further comprises performing an assay to detect Ionized calcium binding adaptor molecule 1 (Iba1) in a specific cell type in the tissue sample, wherein Iba-1 is not detected in the astrocytes comprising CHI3L1. In other words, the CHI3L1-positive astrocytes can be Iba-1-negative.

Another aspect of the present disclosure encompasses a method of categorizing for treatment a subject suspected of having or at risk of having a neurologic disease or disorder. The method comprises performing an assay to detect CHI3L1 and Iba-1 in a specific cell type in a tissue sample obtained from the central nervous system of the subject, wherein the tissue sample comprises grey matter and white matter, and wherein detection of CHI3L1 in astrocytes of the white matter and absence of Iba-1 in the astrocytes comprising CHI3L1 is indicative of ALS in the subject, and the subject is confirmed as a candidate for ALS treatment.

Yet another aspect of the present disclosure encompasses a method of determining a treatment protocol for a subject suspected of having or at risk of having a neurological disease or disorder. The method comprises performing an assay to detect CHI3L1 in a specific cell type in a tissue sample obtained from the central nervous system of the subject, wherein the tissue sample comprises grey matter and white matter, and assigning an ALS treatment protocol to the subject if CHI3L1 is detected in astrocytes of the white matter, CHI3L1 is not detected in microglia of the white matter, and CHI3L1 is not detected in cells of the grey matter, wherein the neurological treatment protocol comprises administering an anti-neuroinflammatory agent to the subject.

In some aspects the method further comprises performing an assay to detect Iba-1 in a specific cell type in the tissue sample, wherein Iba-1 is not detected in the astrocytes comprising CHI3L1.

Another aspect of the present disclosure encompasses a method of determining a treatment protocol for a subject having a neurological disease or disorder. The method comprises performing an assay to detect CHI3L1 in a specific cell type in a tissue sample obtained from the central nervous system of the subject, wherein the tissue sample comprises grey matter and white matter, and assigning an ALS treatment protocol to the subject if CHI3L1 is detected in astrocytes of the white matter, CHI3L1 is not detected in microglia of the white matter, and CHI3L1 is not detected in cells of the grey matter, wherein the neurological treatment protocol comprises administering an anti-neuroinflammatory agent to the subject.

In some aspects the method further comprises performing an assay to detect Iba-1 in a specific cell type in the tissue sample, wherein Iba-1 is not detected in the astrocytes comprising CHI3L1.

An additional aspect of the present disclosure encompasses a method of monitoring the therapeutic effect of an ALS treatment protocol in a subject being treated with the ALS treatment protocol. The method comprises performing an assay to detect CHI3L1 in a specific cell type in a first tissue sample obtained from the central nervous system of the subject, performing an immunostaining assay to detect CHI3L1 in a specific cell type in a second tissue sample obtained from the central nervous system of the subject at a period of time after the first tissue sample is obtained, wherein the tissue sample comprises grey matter and white matter, and comparing the number of astrocytes detected in the white matter in the first and second tissue samples. A decreased or maintained number of astrocytes comprising CHI3L1 in the second sample relative to the first sample is indicative that the treatment protocol is therapeutically effective in the subject.

In some aspects the method further comprises performing an assay to detect Iba-1 in a specific cell type in the tissue sample, wherein Iba-1 is not detected in the astrocytes comprising CHI3L1.

One aspect of the present disclosure encompasses methods of determining post-mortem if a deceased subject had a neurological disease or disorder. The method comprises performing an immunostaining assay to detect CHI3L1 in a specific cell type in a tissue sample obtained from the central nervous system of the subject, wherein the tissue sample comprises grey matter and white matter. Detection of CHI3L1 in astrocytes of the white matter, absence of CHI3L1 in microglia of the white matter, and absence of CHI3L1 in cells of the grey matter is indicative of ALS in the deceased subject.

In any of the methods, the astrocytes in which CHI3L1 was detected can be astrocytes that contain or express glial fibrillary acidic protein (GFAP; GFAP-positive). Further, in any of the methods, the tissue sample can be a sample obtained from the motor cortex.

Methods of detecting the presence of a protein such as CHI3L1, Iba-1, and GFAP in a cell type are known in the art and generally include a signaling molecule in combination with a targeting moiety that guides or targets the signaling molecule to the protein to be detected. Non-limiting examples of targeting moieties include antibodies, antibody fragments, peptides, small molecules, polysaccharides, nucleic acids, aptamers, peptidomimetics, other mimetics and drugs alone or in combination. Signaling molecules can be luminescent molecules, chemiluminescent molecules, fluorochromes, fluorescent quenching agents, colored molecules, radioisotopes, scintillants, enzymes such as alkaline phosphatase, peroxidase, and luciferase, and colorimetric substrates. The skilled artisan would readily recognize other useful labels that are not mentioned above, which may be employed in detecting the presence of a protein in a specific cell type. In any of the methods, an assay to detect a protein such as CHI3L1, Iba-1, and GFAP in a specific cell type can be an immunostaining assay. In some aspects, the immunostaining assay is an immunohistochemical assay.

II. Kits

A further aspect of the present disclosure provides immunoassay kits for conducting an assay for detecting one or more chitinase proteins in a biological sample. In some aspects, the immunoassay is as described in Section I(a). In some aspects, the assay is an enzyme linked immunosorbant assay (ELISA). In some aspects, the biological sample is a CSF. In other aspects, the biological sample is plasma. In some aspects, the chitinase is Chit-1, CHI3L1, or combinations thereof.

A further aspect of the present disclosure provides immunostaining kits for conducting immunohistochemical assays for detecting CHI3L1 in a specific cell type in a tissue sample obtained from the central nervous system of a subject. In some aspects, the assay is an immunostaining assay.

The kits provided herein generally include instructions for carrying out the methods detailed below. Instructions included in the kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

The term "neurologic disease or disorder" refers broadly to dysfunction in the CNS and/or peripheral nervous system of a mammal, caused by or related to inflammation. "Neurological disease or disorder" as used herein encompasses but is not limited to ALS, Alzheimer's disease, Parkinson's disease, brain metastases, viral encephalitis, neuropathy, multiple sclerosis, upper motor neuron disease, primary lateral sclerosis, chronic inflammatory demyelinating polyneuropathy, idiopathic sensorimotor polyneuropathy, spinocerebellar ataxia, lymphoma, and lower motor neuron disease.

The term "biological fluid" refers to any fluid produced by an organism including an animal and a cell. Non-limiting examples of a biological fluid are serum, plasma, urine, whole blood, saliva, interstitial fluid, cytosol, cell extract and tissue extract.

The term "subject" refers to any mammal, including a human, non-human primate, dog, rat, mouse, or guinea pig which suffers, is suspected of or is at risk of suffering from a neurologic disease or disorder, whether occurring naturally or induced for experimental purposes.

As used herein, the administration of an agent or drug to a subject or patient includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the term "treating" refers to: (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures. In the context of ALS spectrum disorder, "treat" and "treating" encompass alleviating, ameliorating, delaying the onset of, inhibiting the progression of, or reducing the severity of one or more symptoms associated with ALS.

As used herein, "therapeutically effective amount" or "pharmaceutically active dose" refers to an amount of a composition which is effective in treating the named disease, disorder or condition.

The terms "sensitivity" and "specificity" are statistical measures of the performance of a binary classification test. Sensitivity (also called the true positive rate, the recall, or probability of detection in some fields) measures the proportion of actual positives that are correctly identified as such (e.g., the percentage of sick people who are correctly identified as having the condition). Specificity (also called the true negative rate) measures the proportion of actual negatives that are correctly identified as such (e.g., the percentage of healthy people who are correctly identified as not having the condition). The terms "positive" and "negative" do not refer to the value of the condition of interest, but to its presence or absence. The condition itself could be a disease, so that "positive" might mean "diseased," while "negative" might mean "healthy". In many tests, including diagnostic medical tests, sensitivity is the extent to which actual positives are not overlooked (so false negatives are few), and specificity is the extent to which actual negatives are classified as such (so false positives are few). As such, a highly sensitive test rarely overlooks an actual positive (for example, overlooking a disease condition), a highly specific test rarely registers a positive classification for anything that is not the target of testing (for example, diagnosing a disease condition in a healthy subject), and a test that is highly sensitive and highly specific does both.

As various changes could be made in the above-described cells and methods without departing from the scope of the invention, it is intended that all matter contained in the above description and in the examples given below shall be interpreted as illustrative and not in a limiting sense.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Cross-Sectional Analysis of Chit-1 and CHI3L1 in ALS and Controls

Figure 1B:
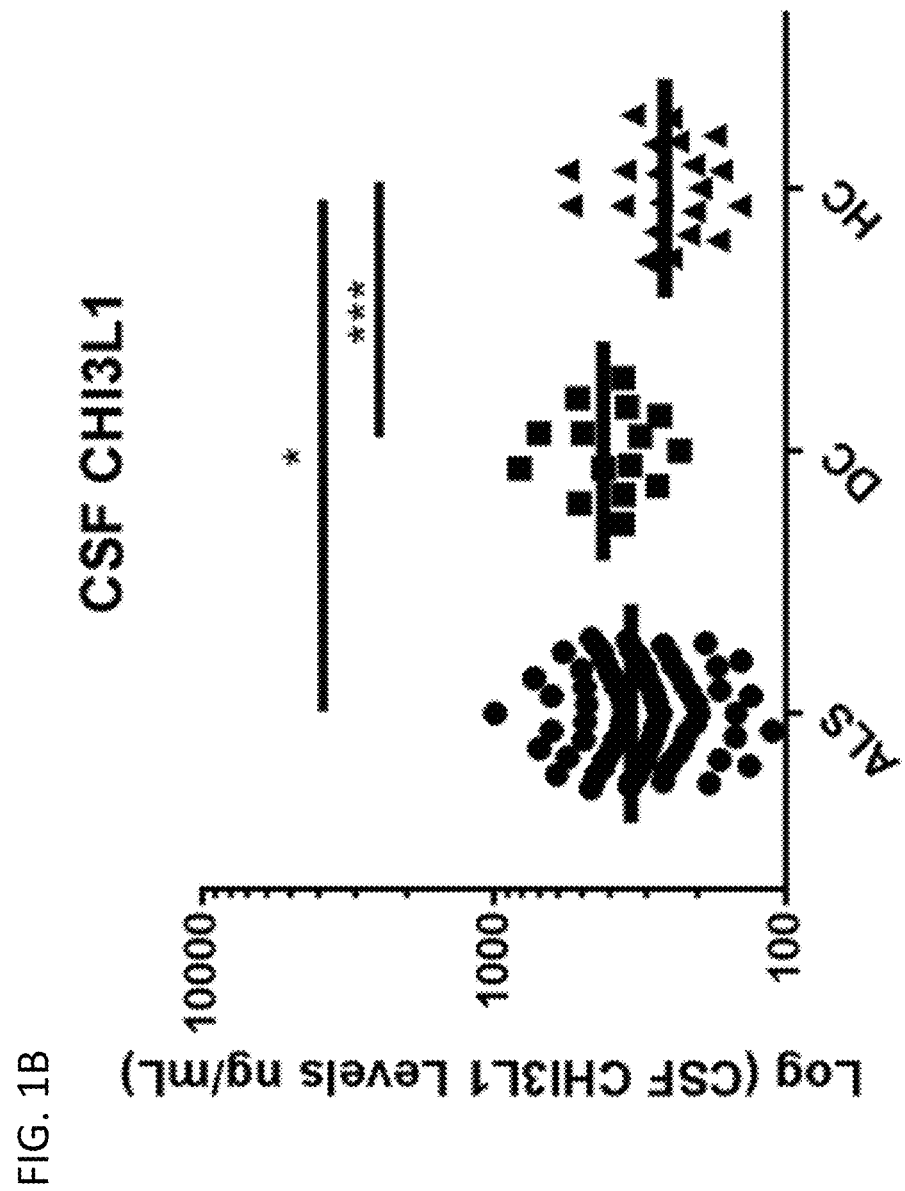
FIG. 1B. Concentration of CSF CHI3L1 using data from baseline visits for ALS patients, disease controls (DC), and healthy controls (HC). *$p<0.05$, $p<0.01$, *$p<0.001$, ****$p<0.0001$, and NS=not significant.
Figure 1C:
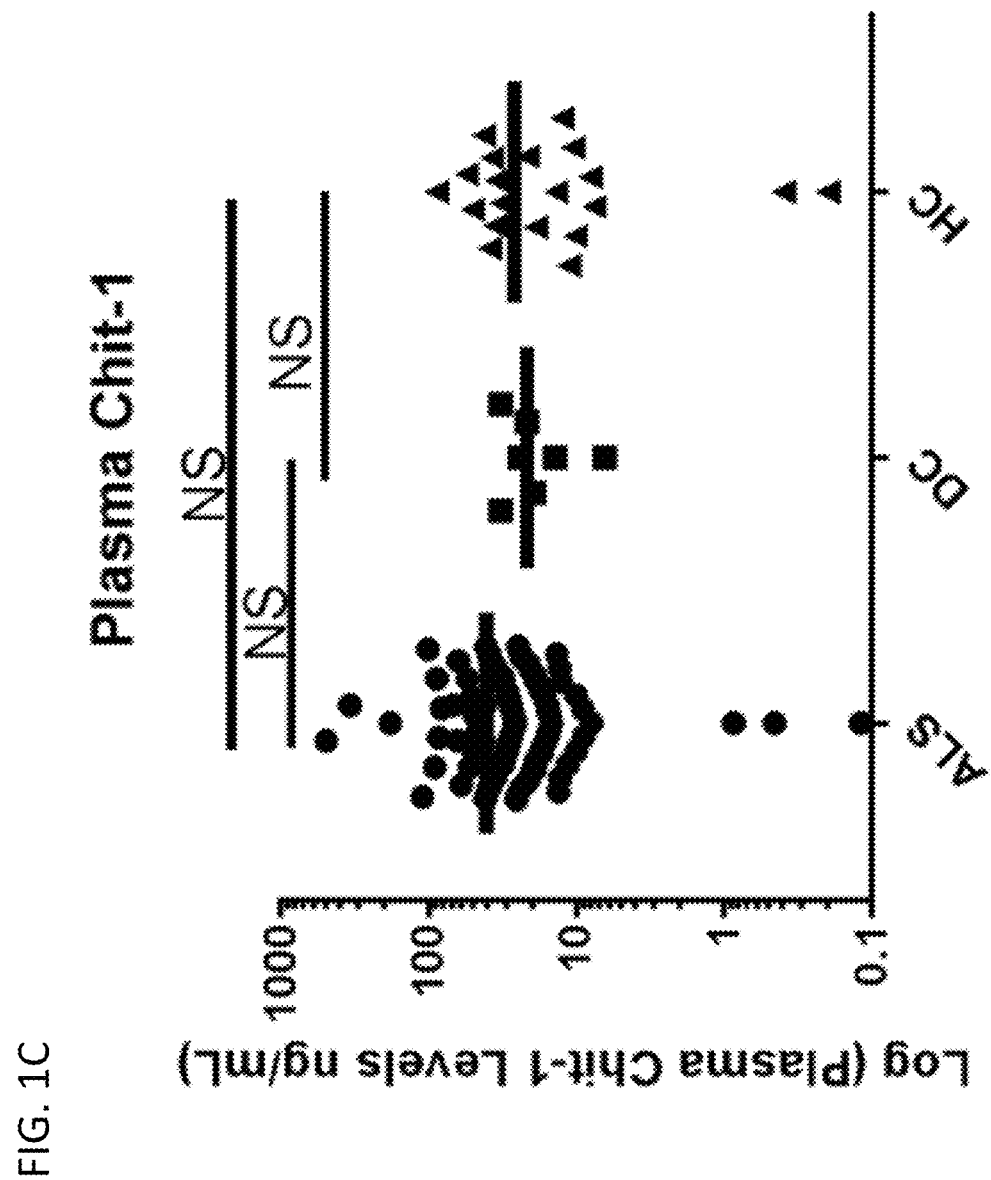
FIG. 1C. Concentration of plasma Chit-1 using data from baseline visits for ALS patients, disease controls (DC), and healthy controls (HC). *$p<0.05$, $p<0.01$, *$p<0.001$, ****$p<0.0001$, and NS=not significant.
Figure 1D:
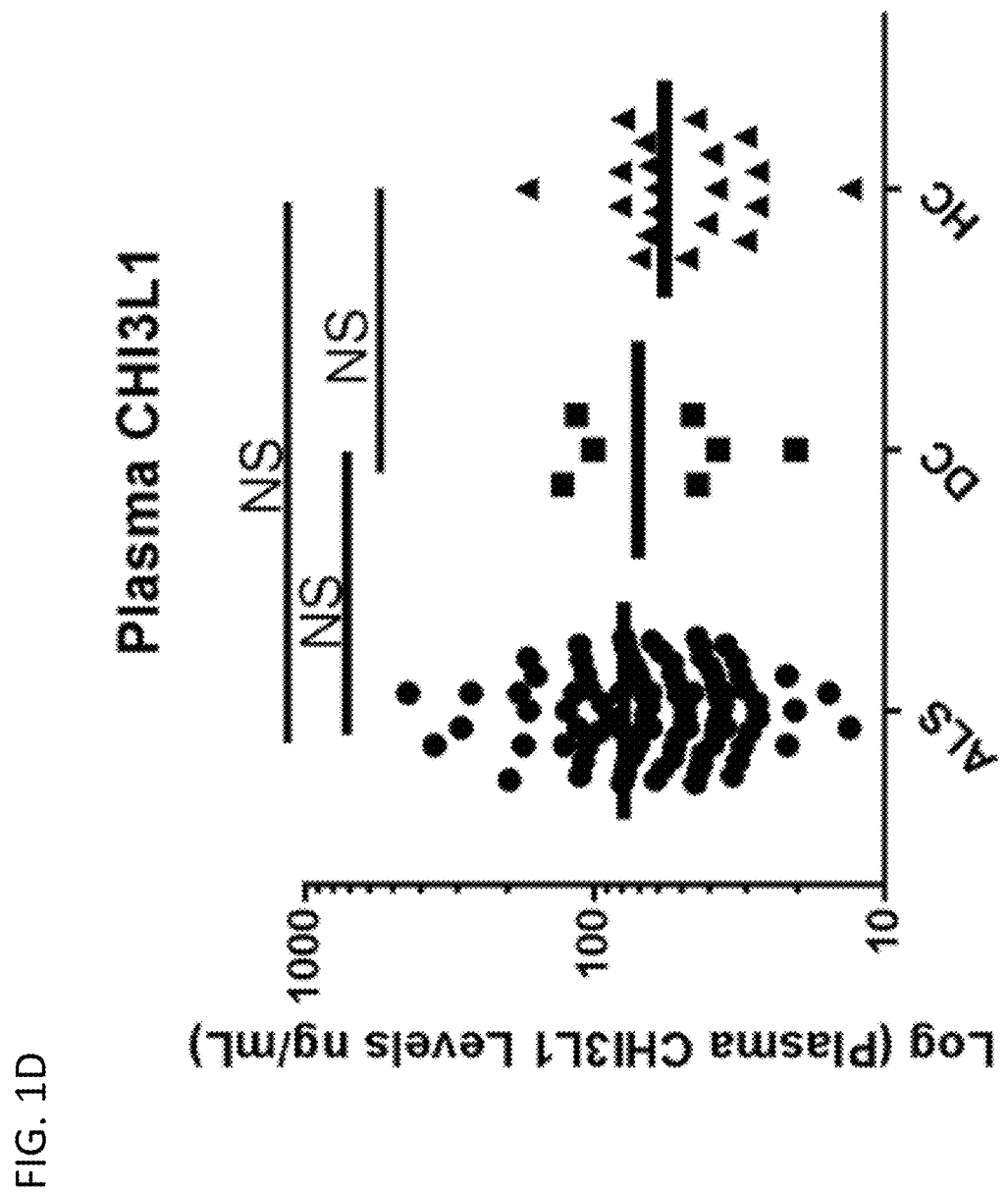
FIG. 1D. Concentration of plasma CHI3L1 using data from baseline visits for ALS patients, disease controls (DC), and healthy controls (HC). *$p<0.05$, $p<0.01$, *$p<0.001$, ****$p<0.0001$, and NS=not significant.
Figure 7A:
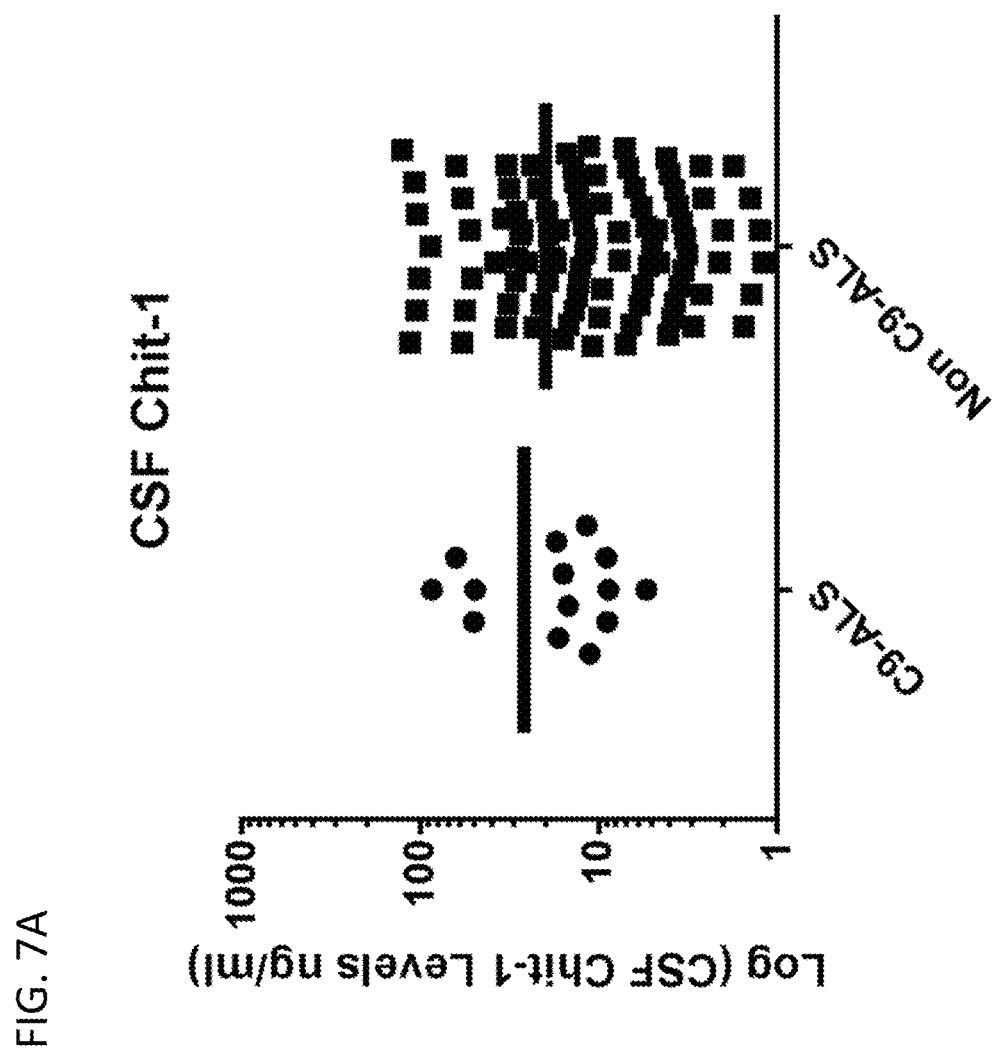
FIG. 7A. Cross-sectional analysis of (A) CSF Chit-1, (B) CSF CHI3L1, (C) Plasma Chit-1, and (D) Plasma CHI3L1 using data from baseline visits for patients with the C9orf72 repeat expansion (C9-ALS) as compared to all other ALS patients (Non C9-ALS). Mann Whitney U test was used to assess differences between pairwise comparisons. *=$p<0.05$.
Figure 7B:
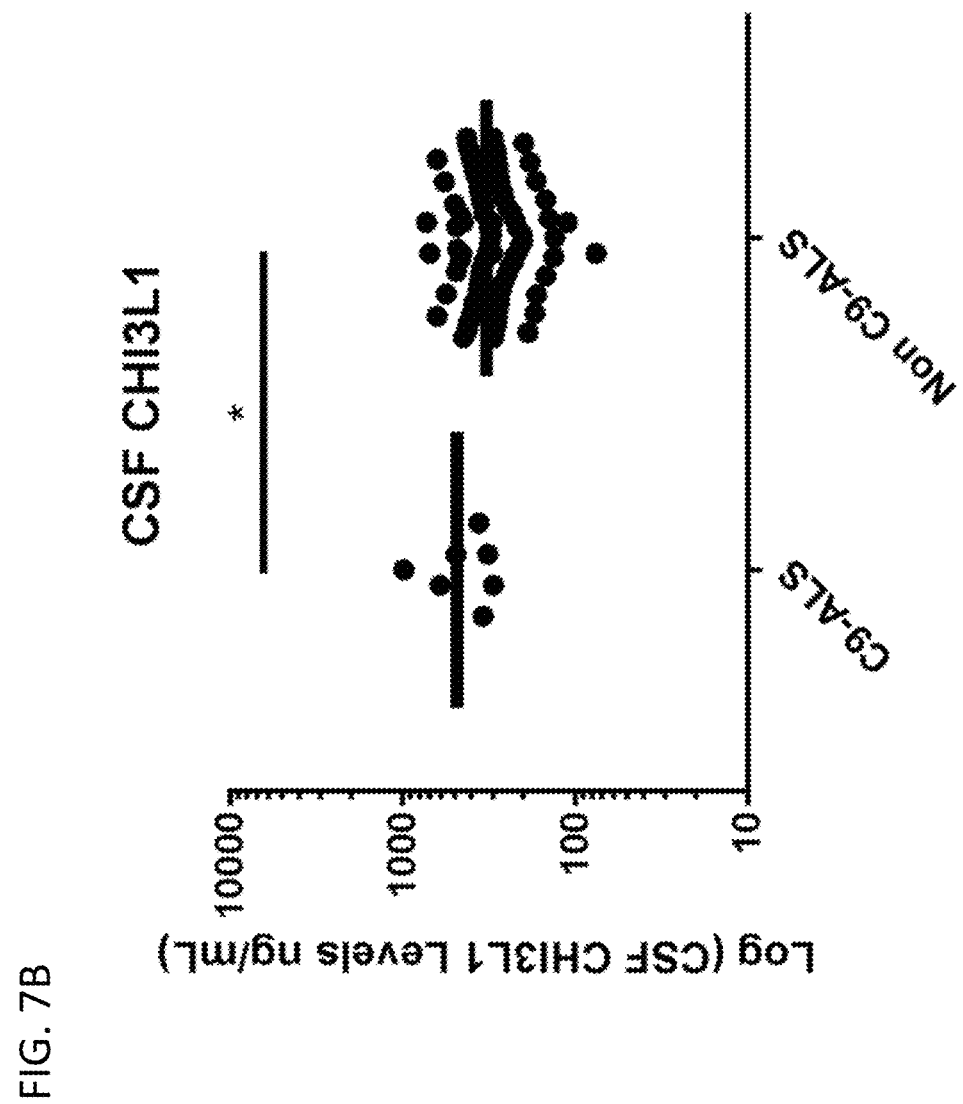
FIG. 7B. Cross-sectional analysis of (A) CSF Chit-1, (B) CSF CHI3L1, (C) Plasma Chit-1, and (D) Plasma CHI3L1 using data from baseline visits for patients with the C9orf72 repeat expansion (C9-ALS) as compared to all other ALS patients (Non C9-ALS). Mann Whitney U test was used to assess differences between pairwise comparisons. *=$p<0.05$.
Figure 7C:
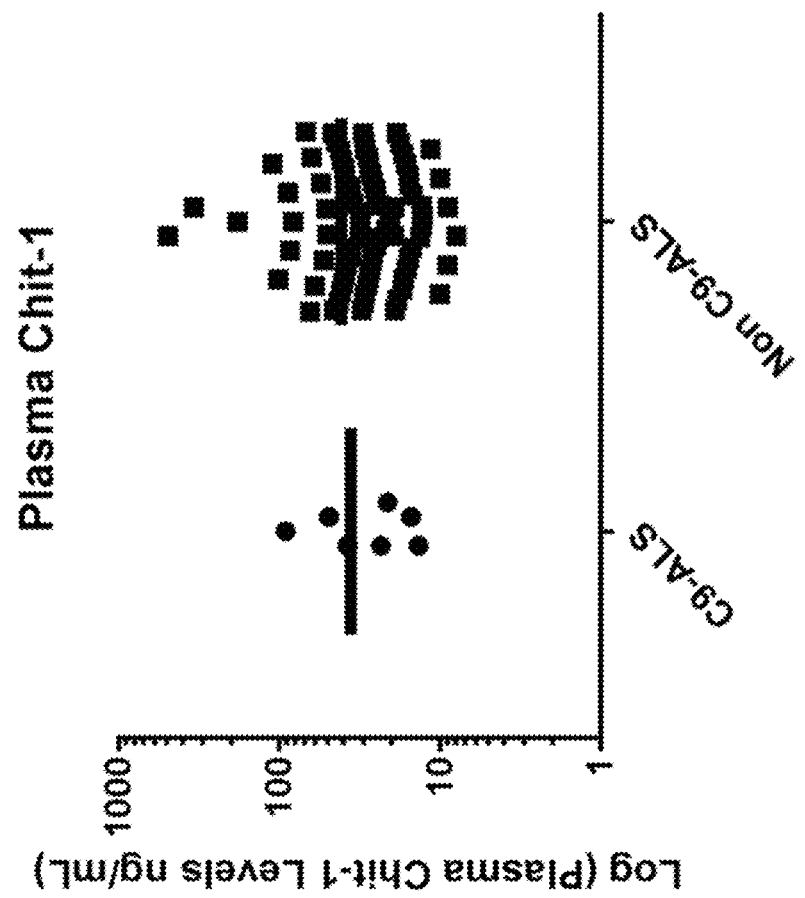
FIG. 7C. Cross-sectional analysis of (A) CSF Chit-1, (B) CSF CHI3L1, (C) Plasma Chit-1, and (D) Plasma CHI3L1 using data from baseline visits for patients with the C9orf72 repeat expansion (C9-ALS) as compared to all other ALS patients (Non C9-ALS). Mann Whitney U test was used to assess differences between pairwise comparisons. *=p<0.05.
Figure 7D:
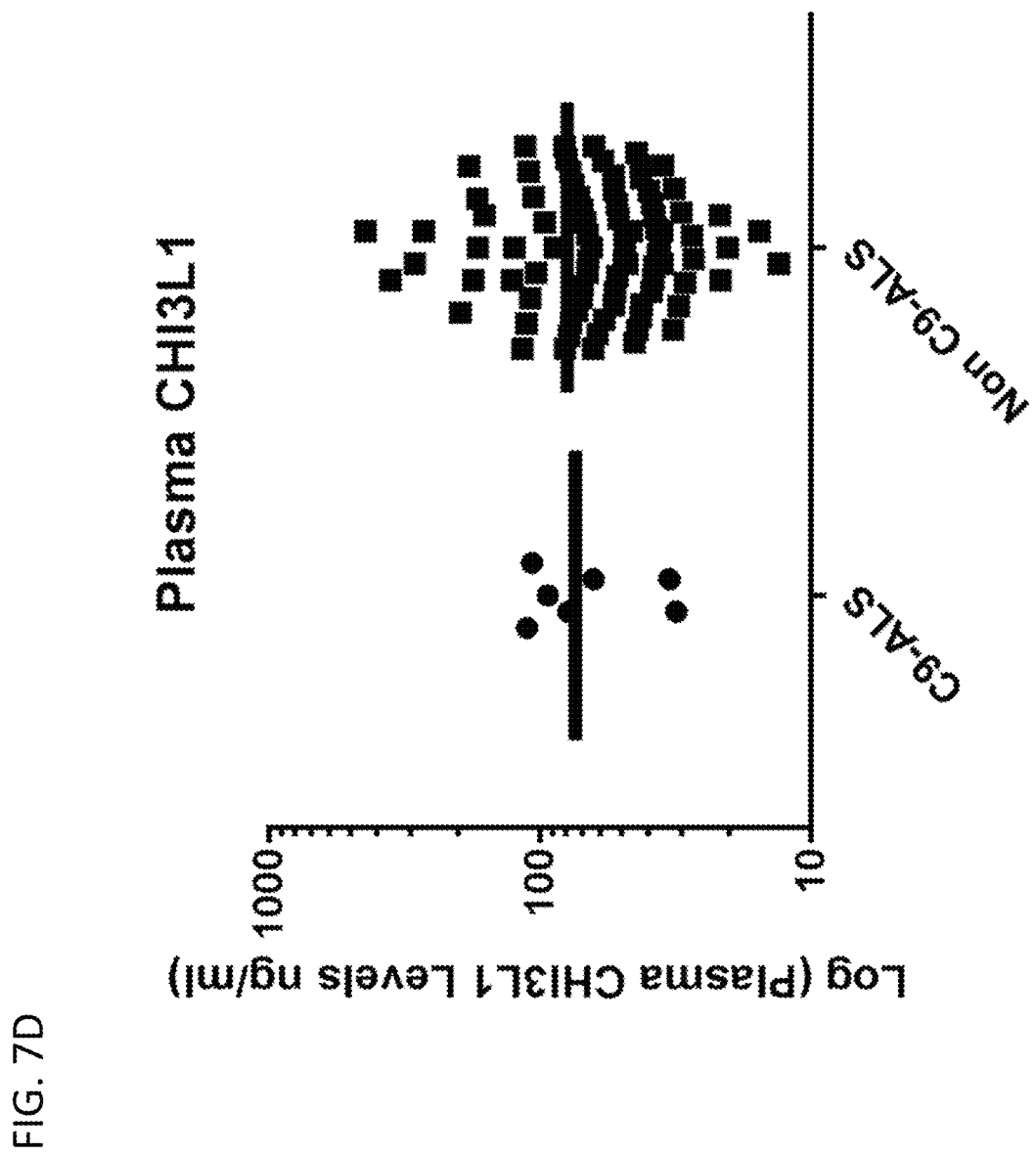
FIG. 7D. Cross-sectional analysis of (A) CSF Chit-1, (B) CSF CHI3L1, (C) Plasma Chit-1, and (D) Plasma CHI3L1 using data from baseline visits for patients with the C9orf72 repeat expansion (C9-ALS) as compared to all other ALS patients (Non C9-ALS). Mann Whitney U test was used to assess differences between pairwise comparisons. *=p<0.05.

Increased abundance of Chit-1, CHI3L1 and CHI3L2 in ALS CSF as compared to healthy control subjects (HCs) by mass spectrometry-based proteomics was previously identified by the inventors. In the current study, these results were confirmed by measuring levels of Chit-1 and CHI3L1 in CSF and plasma by ELISA. CSF Chit-1 levels were significantly higher in ALS patients compared to both disease controls (DCs) and HCs (FIG. 1A). Levels of CSF CHI3L1 were also higher in ALS patients compared to HCs but not DCs (FIG. 1B). Increased CHI3L1 levels were also detected in DCs as compared to HCs. Levels of Chit-1 and CHI3L1 were assessed in matching plasma samples but no significant differences were observed among groups for either chitinase (FIGS. 1C-D). Additionally, neither Chit-1 nor CHI3L1 levels differed between sex or site of disease onset. Interestingly, CHI3L1 but not Chit-1 levels were significantly higher in CSF from patients with the C9orf72 repeat expansion (C9-ALS) as compared to non-C9-ALS cases (FIG. 7B).

Figure 1E:
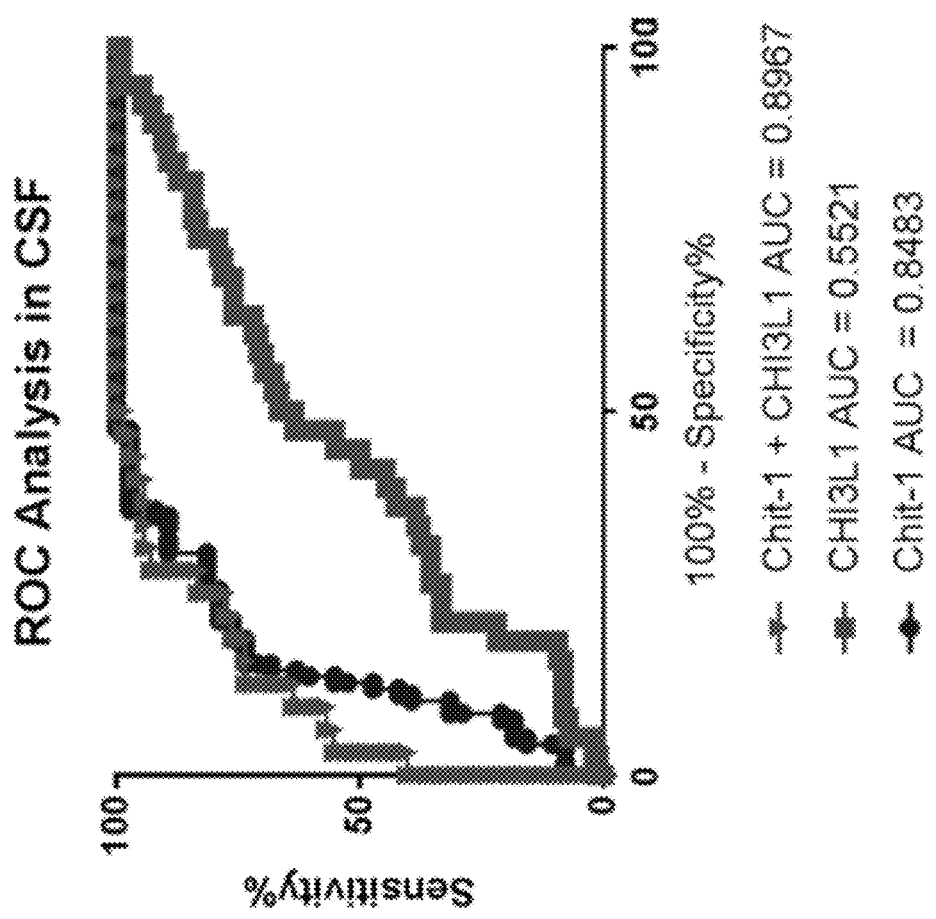
FIG. 1E. Receiver operator characteristic (ROC) curves using baseline measures of CSF for Chit-1 (blue circles), CHI3L1 (red squares), and the combination of Chit-1 and CHI3L1 (purple triangles), comparing ALS to DC and HCs.

To assess if Chit-1 or CHI3L1 could distinguish between ALS and the combined control group, ROC curve analyses were employed. CSF Chit-1 levels discriminated ALS patients and controls with an area under the curve (AUC) of 0.8483, p<0.0001 while CSF CHI3L1 performed poorly with an AUC of 0.5521, p=0.34 (FIG. 1E). Based on the highest Youden's index, a cutoff value of greater than 6.24 ng/mL of CSF Chit-1 yielded a sensitivity of 63.6% (95% CI 54.2%-72.2%) and a specificity of 97.4% (95 CI 86.2%-99.9%). At a cutoff value greater than 281.3 ng/mL of CSF CHI3L1, we observed a sensitivity of 66.3% (95% CI 55.9%-75.7%) and a specificity of 50% (95 CI 33.4%-

Figure 1F:
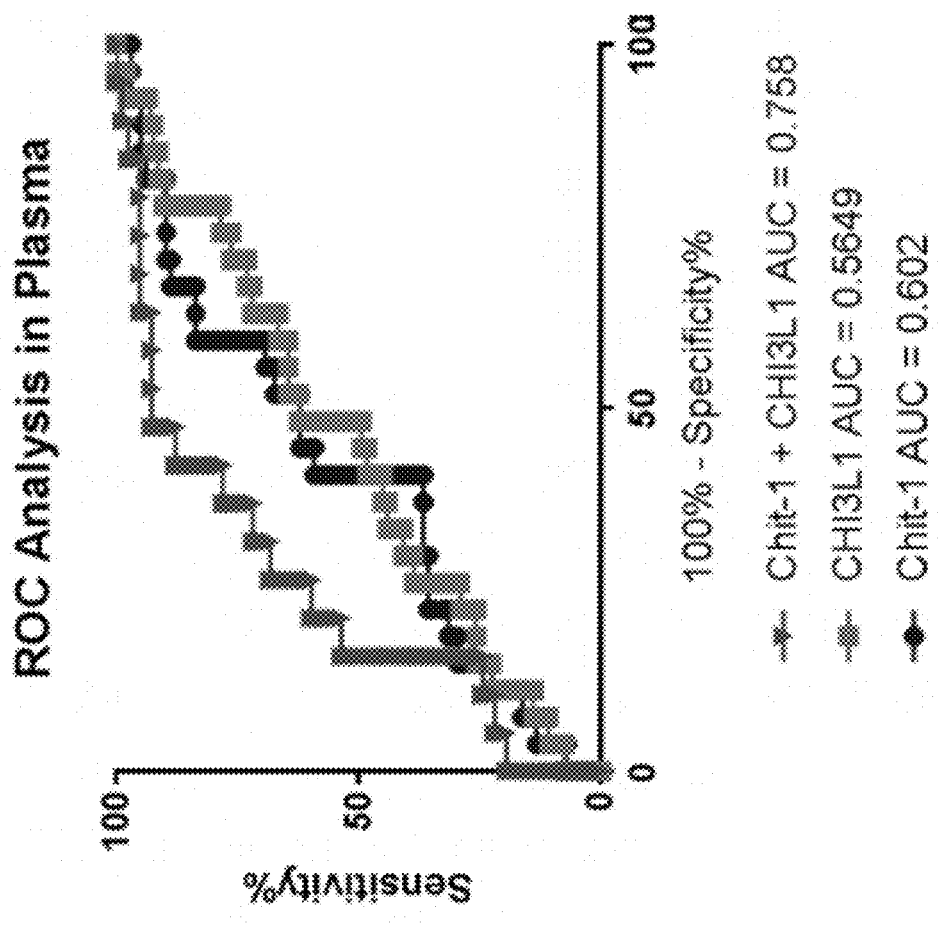
FIG. 1F. Receiver operator characteristic (ROC) curves using baseline measures of plasma for Chit-1 (blue circles), CHI3L1 (red squares), and the combination of Chit-1 and CHI3L1 (purple triangles), comparing ALS to DC and HCs.

66.3%). Upon combining the two biomarkers, no significant improvement in performance was achieved over Chit-1 alone (AUC Chit-1+CHI3L1=0.8967 vs. AUC Chit-1=0.8483, p=0.05), but performance was improved over CHI3L1 alone (AUC Chit-1+CHI3L1=0.8967 vs. AUC CHI3L1=0.5521, p<0.01) (FIG. 1E). Similar analysis was performed using plasma levels of Chit-1 and CHI3L1. The plasma AUC values were 0.602 (p=0.1053) for Chit-1, 0.5649 (p=0.3057) for CHI3L1, and 0.758 (p=0.0005) for the combination of Chit-1 and CHI3L1 (FIG. 1F). The combination of plasma Chit-1 and CHI3L1 significantly improved performance as compared to each biomarker alone (AUC Chit-1+CHI3L1 vs. either AUC Chit-1 alone or AUC CHI3L1 alone, p<0.01).

Example 2. Correlations Between Chitinases and Clinical Measures of ALS

Figure 8B:
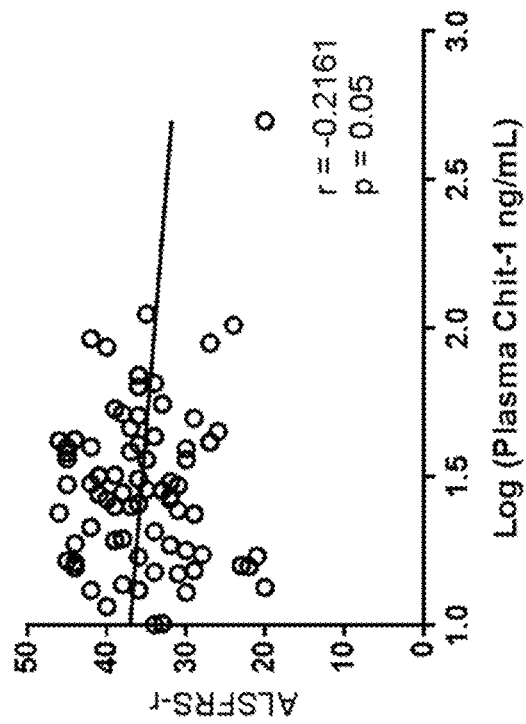
FIG. 8B. Correlation analysis between ALSFRS-r at baseline visit and plasma Chit-1. Pearson's correlation coefficient (r) was used for all pair-wise analyses, with p<0.05 considered significant.
Figure 8A:
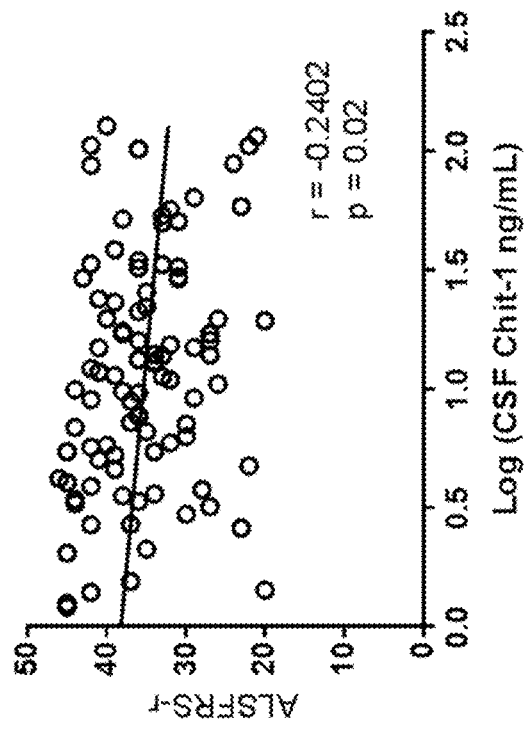
FIG. 8A. Correlation analysis between ALSFRS-r at baseline visit and CSF Chit-1. Pearson's correlation coefficient (r) was used for all pair-wise analyses, with p<0.05 considered significant.
Figure 8D:
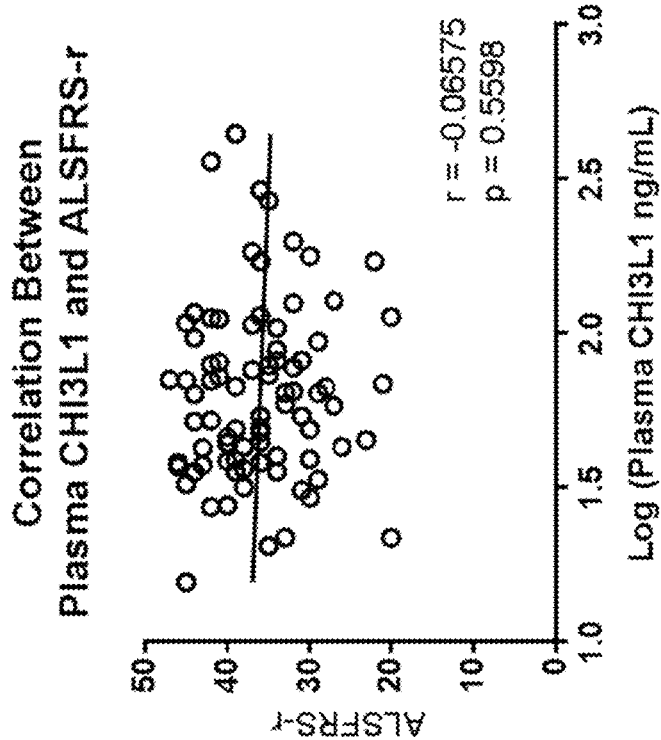
FIG. 8D. Correlation analysis between ALSFRS-r at baseline visit and plasma CHI3L1. Pearson's correlation coefficient (r) was used for all pair-wise analyses, with p<0.05 considered significant.
Figure 8C:
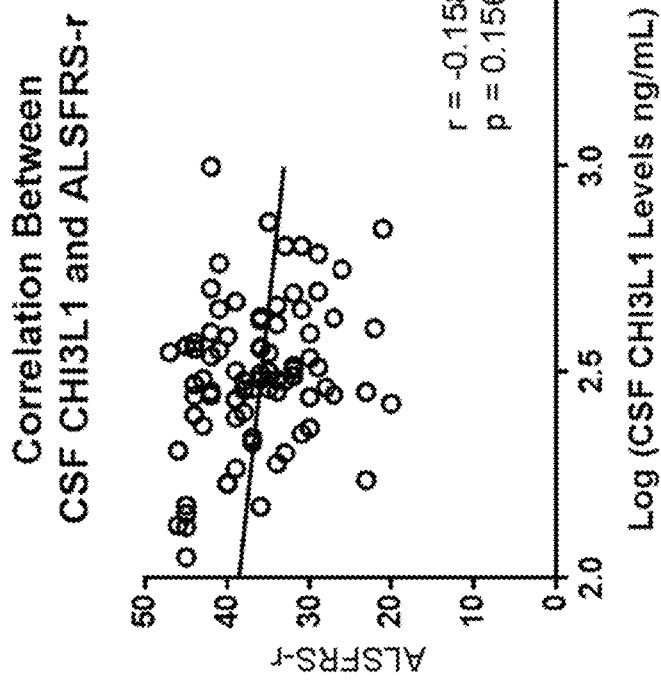
FIG. 8C. Correlation analysis between ALSFRS-r at baseline visit and CSF CHI3L1. Pearson's correlation coefficient (r) was used for all pair-wise analyses, with p<0.05 considered significant.
Figures 8E, 8F:
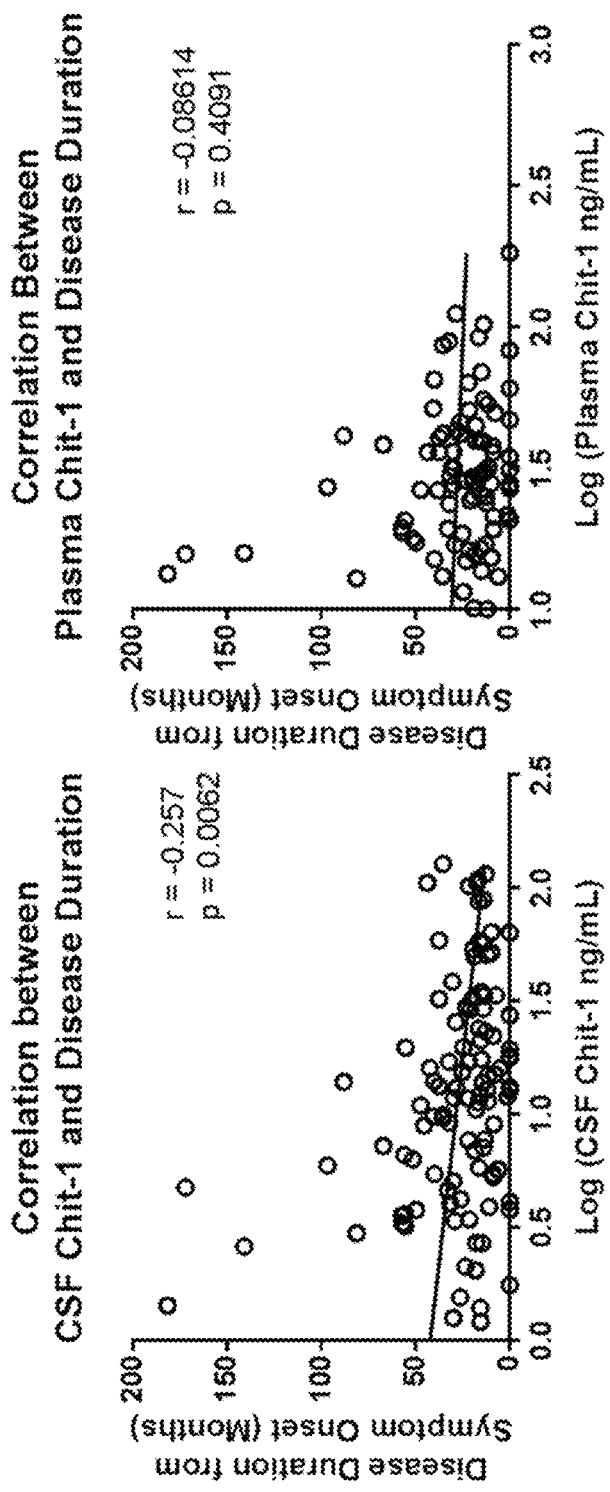
FIG. 8E. Correlation analysis between disease duration (months from symptom onset to draw date) and CSF Chit-1. Pearson's correlation coefficient (r) was used for all pair-wise analyses, with p<0.05 considered significant.
FIG. 8F. Correlation analysis between disease duration (months from symptom onset to draw date) and plasma Chit-1. Pearson's correlation coefficient (r) was used for all pair-wise analyses, with p<0.05 considered significant.
Figure 8H:
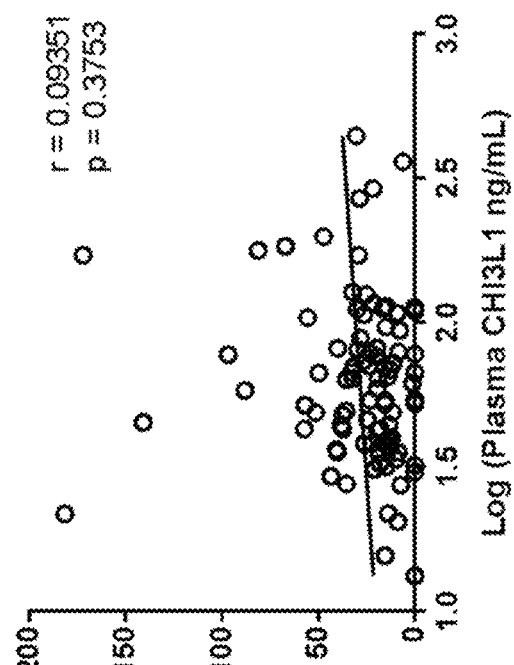
FIG. 8H. Correlation analysis between disease duration (months from symptom onset to draw date) and plasma CHI3L1. Pearson's correlation coefficient (r) was used for all pair-wise analyses, with p<0.05 considered significant.
Figure 8G:
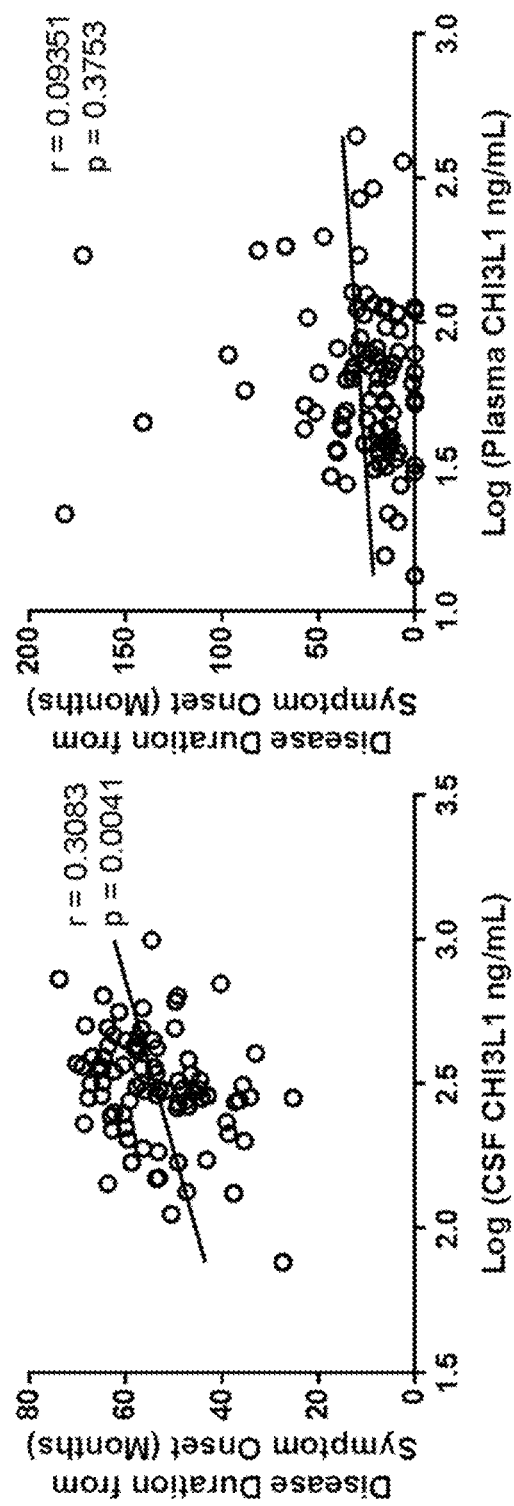
FIG. 8G. Correlation analysis between disease duration (months from symptom onset to draw date) and CSF CHI3L1. Pearson's correlation coefficient (r) was used for all pair-wise analyses, with p<0.05 considered significant.
Figure 9A:
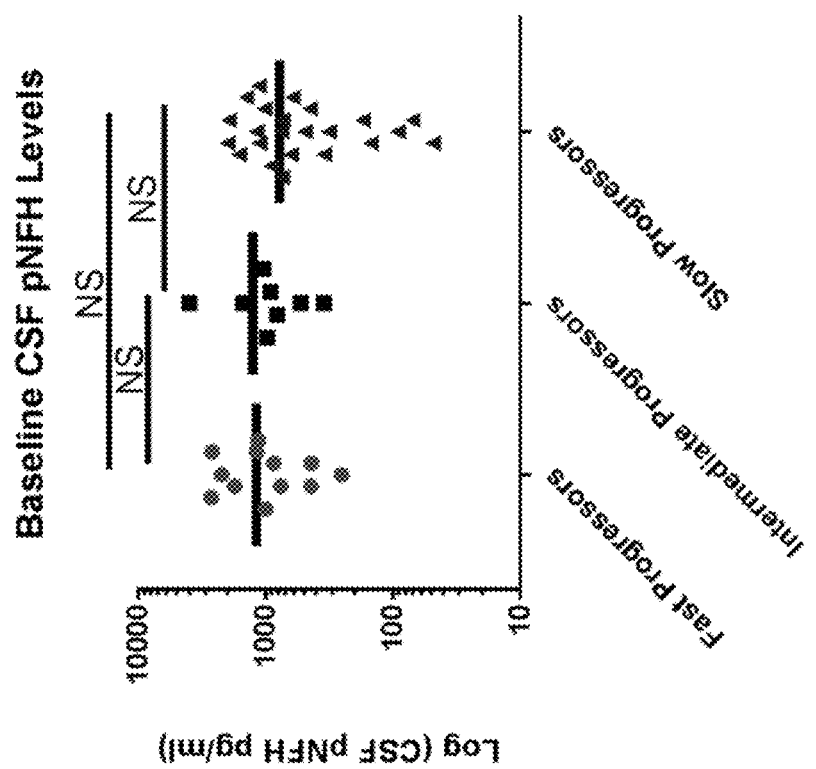
FIG. 9A. Longitudinal measures of pNFH from ALS patients with 3 or more clinic visits and biofluid collection. Baseline levels of CSF pNFH (n=12 FPs, 8 IPs, and 21 SPs) were compared. NS=not significant.
Figure 9B:
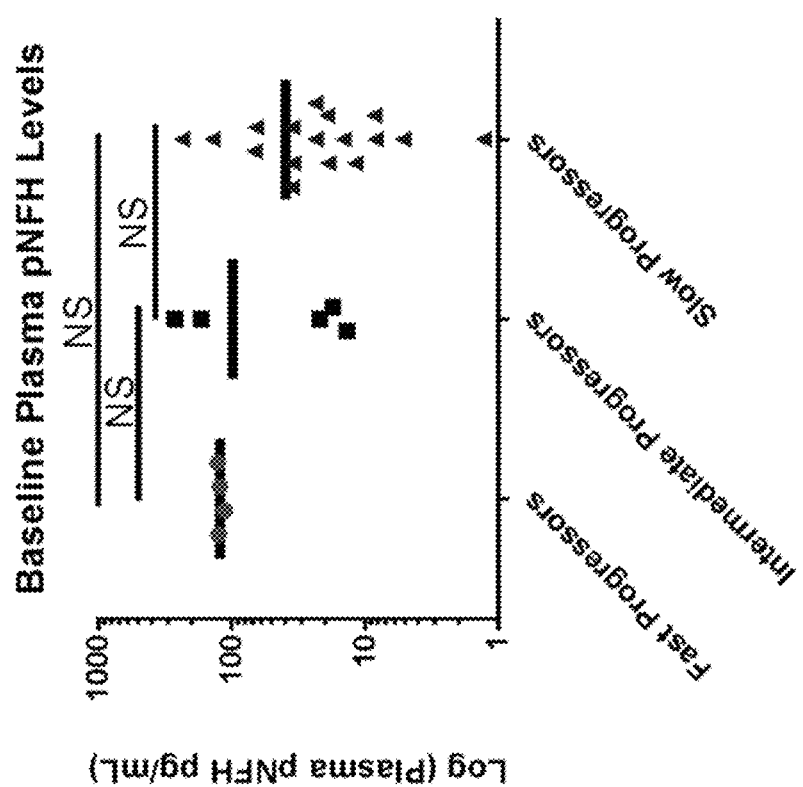
FIG. 9B. Longitudinal levels of CSF pNFH, in which each dotted line represents an individual patient. The solid lines represent the overall linear fit of the longitudinal measurements of pNFH in FPs (red), SPs (blue), and IPs (black). NS=not significant. p-values from linear mixed effects modeling indicate the significance level in which the slopes differ from 0 as assessed by SPSS with p<0.05 being considered significant.
Figure 9C:
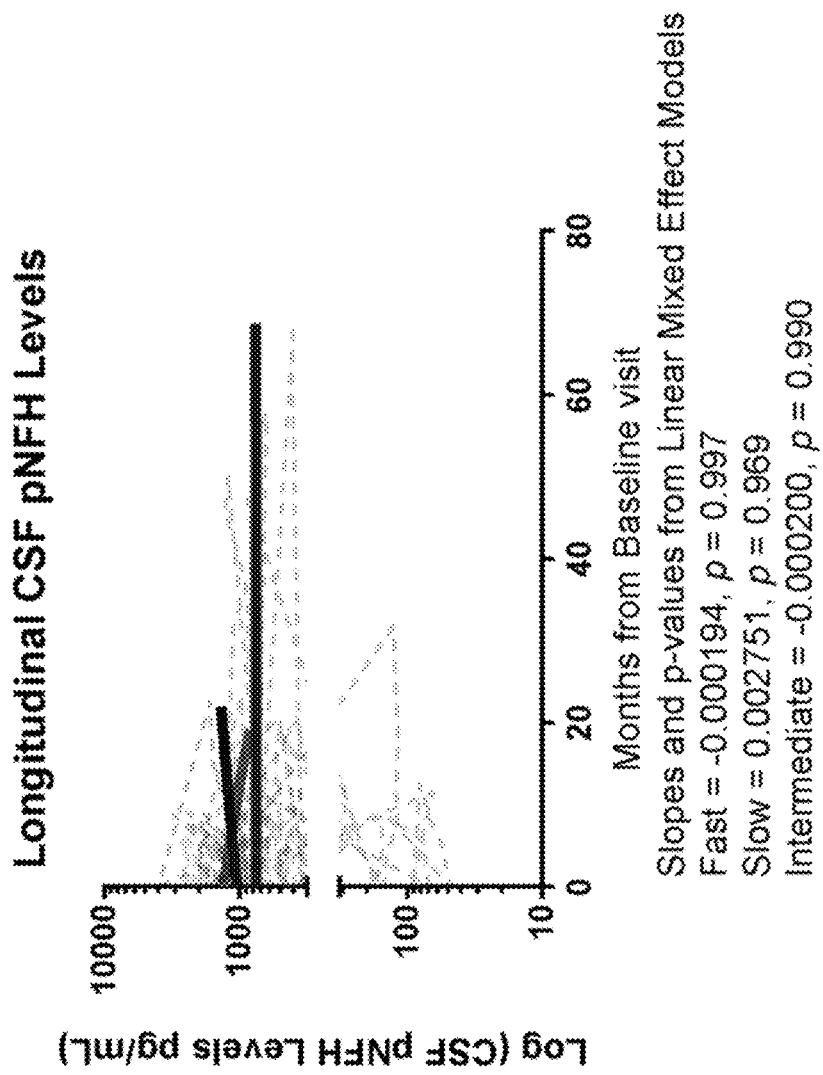
FIG. 9C. Longitudinal measures of pNFH from ALS patients with 3 or more clinic visits and biofluid collection. Baseline levels of plasma pNFH (n=4 FPs, 5 IPs, and 13 SPs) were compared. NS=not significant.
Figure 9D:
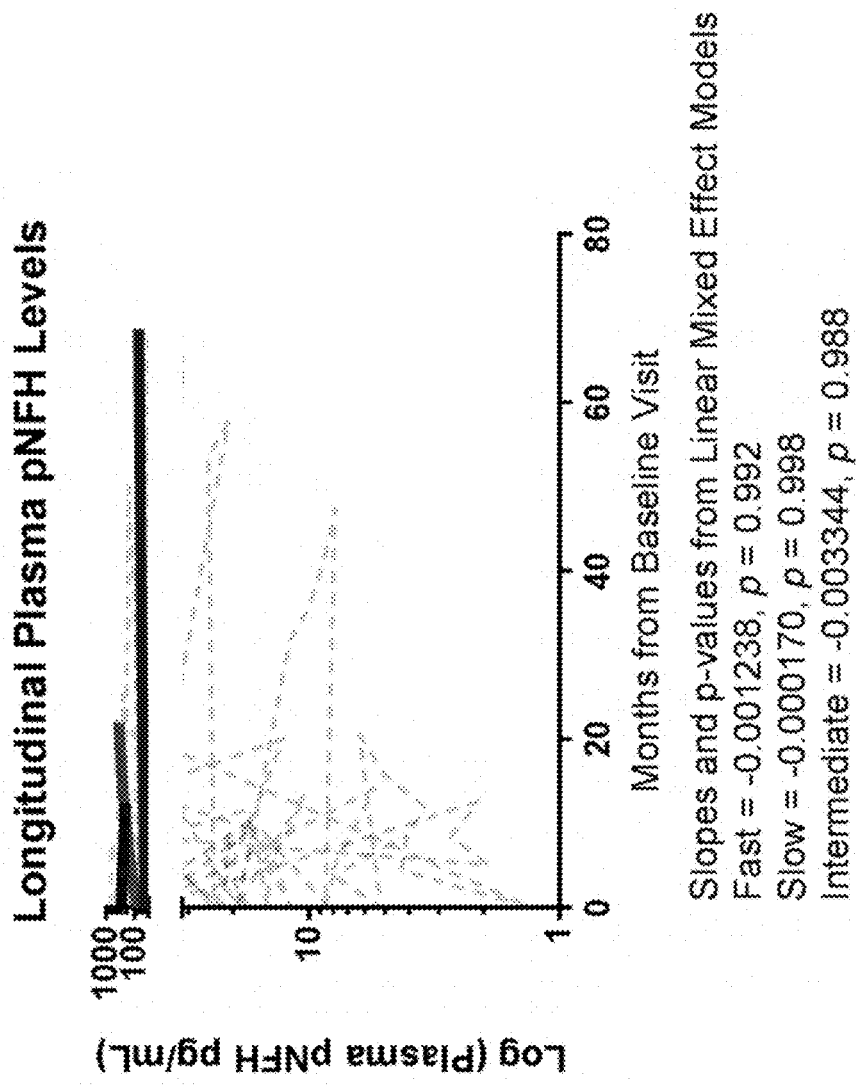
FIG. 9D. Longitudinal levels of plasma pNFH, in which each dotted line represents an individual patient. The solid lines represent the overall linear fit of the longitudinal measurements of pNFH in FPs (red), SPs (blue), and IPs (black). NS=not significant. p-values from linear mixed effects modeling indicate the significance level in which the slopes differ from 0 as assessed by SPSS with p<0.05 being considered significant.

CSF Chit-1 levels were negatively correlated with ALSFRS-r at the baseline visit (FIG. 8A; r=−0.2402, p=0.02). There was no correlation between plasma Chit-1, CSF CHI3L1, or plasma CHI3L1 with ALSFRS-r (FIGS. 8B-D; Plasma Chit-1; r=−0.2161 p=0.05, CSF CHI3L1 r=−0.1581 p=0.1561, and plasma CHI3L1 r=−0.06575 p=0.5598). There was no correlation between plasma Chit-1 and disease duration (FIG. 8F; CSF r=−0.08614, p=0.4091). Similar results were also observed for plasma CHI3L1 (FIG. 8H; r=0.09351 p=0.3753); however, there were correlations between CSF Chit-1 and CHI3L1 with disease duration that reached statistical significance (FIGS. 8E and 8G; Chit-1 r=−0.257 p=0.0062 and CHI3L1 r=0.3083 p=0.0041).

Example 3. Longitudinal Analysis of Chit-1 and CHI3L1

Figure 2A:
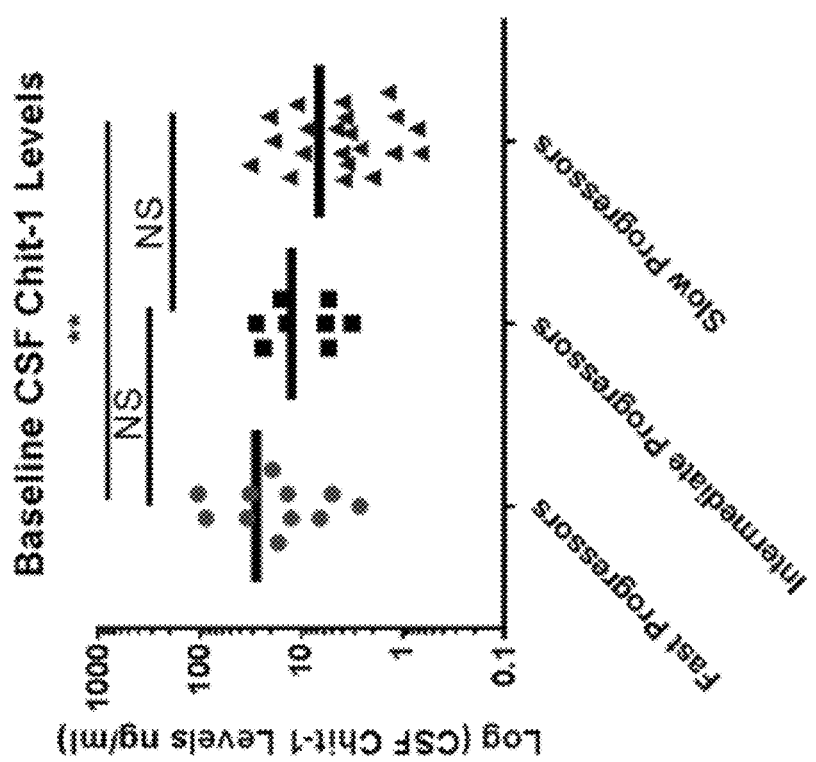
FIG. 2A. Longitudinal measures of chitinases from ALS patients with 3 or more clinic visits and biofluid collection. Baseline levels of CSF Chit-1 (n=11 FPs, 8 IPs, and 23 SPs). The solid lines represent the overall linear fit of the longitudinal measurements of each chitinase in FPs (red), SPs (blue), and IPs (black). **=$p<0.01$; *=$p<0.05$; NS=not significant. p-values from linear mixed effects modeling indicate the significance level in which the slopes differ from 0 as assessed by SPSS with $p<0.05$ being considered significant.
Figure 2B:
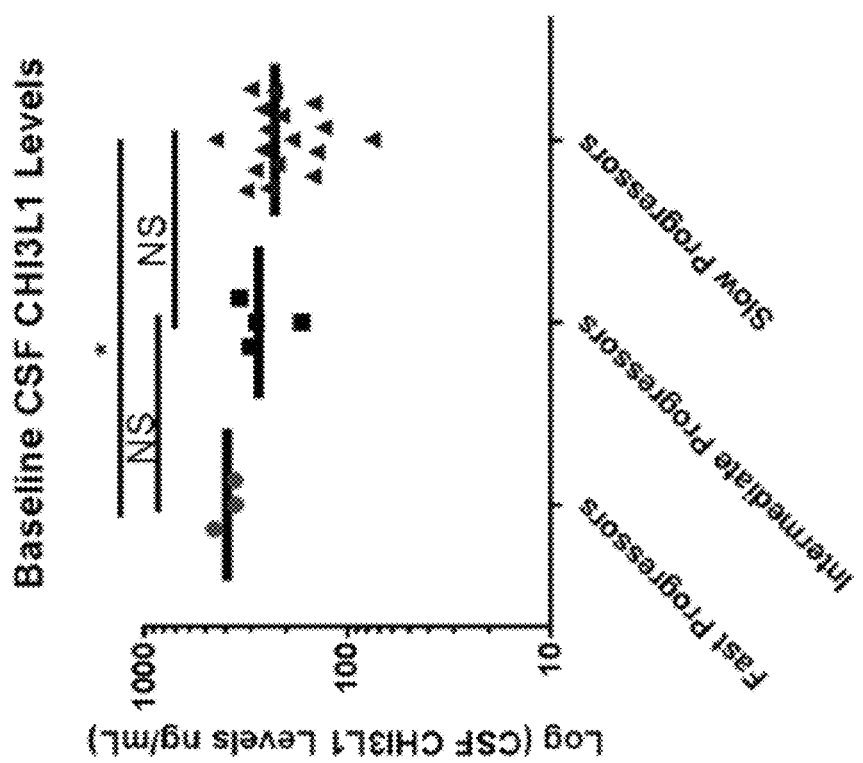
FIG. 2B. Longitudinal measures of chitinases from ALS patients with 3 or more clinic visits and biofluid collection. Baseline levels of CSF CHI3L1 (n=3 FPs, 4 IPs, and 17 SPs). The solid lines represent the overall linear fit of the longitudinal measurements of each chitinase in FPs (red), SPs (blue), and IPs (black). **=$p<0.01$; *=$p<0.05$; NS=not significant. p-values from linear mixed effects modeling indicate the significance level in which the slopes differ from 0 as assessed by SPSS with $p<0.05$ being considered significant.
Figure 2C:
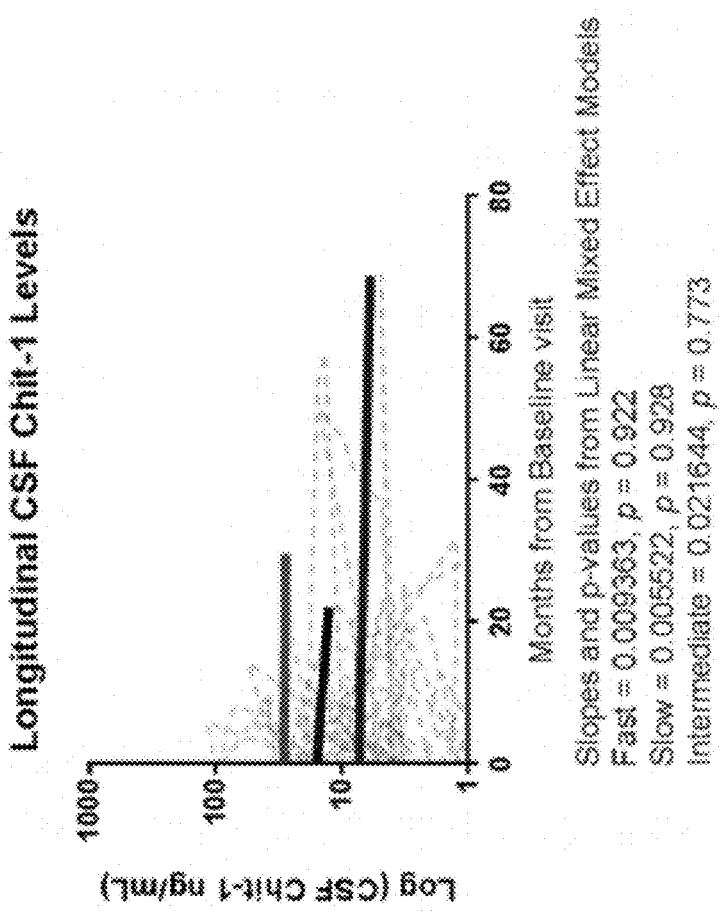
FIG. 2C. Longitudinal levels of CSF Chit-1, in which each dotted line represents an individual patient. The solid lines represent the overall linear fit of the longitudinal measurements of each chitinase in FPs (red), SPs (blue), and IPs (black). **=$p<0.01$; *=$p<0.05$; NS=not significant. p-values from linear mixed effects modeling indicate the significance level in which the slopes differ from 0 as assessed by SPSS with $p<0.05$ being considered significant.
Figure 2D:
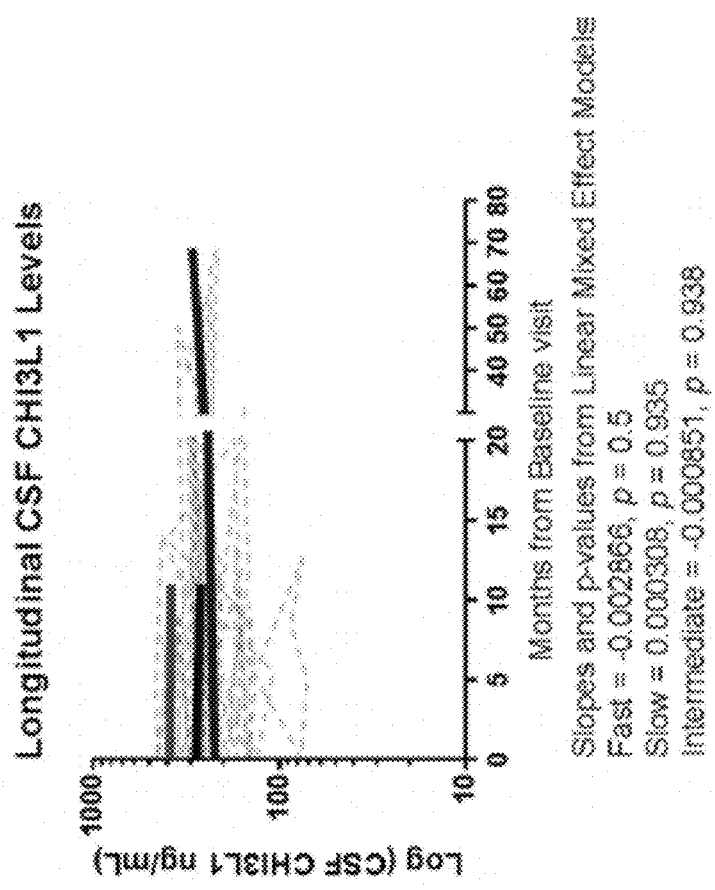
FIG. 2D. Longitudinal levels of CSF CHI3L1, in which each dotted line represents an individual patient. The solid lines represent the overall linear fit of the longitudinal measurements of each chitinase in FPs (red), SPs (blue), and IPs (black). **=$p<0.01$; *=$p<0.05$; NS=not significant. p-values from linear mixed effects modeling indicate the significance level in which the slopes differ from 0 as assessed by SPSS with $p<0.05$ being considered significant.
Figure 2E:
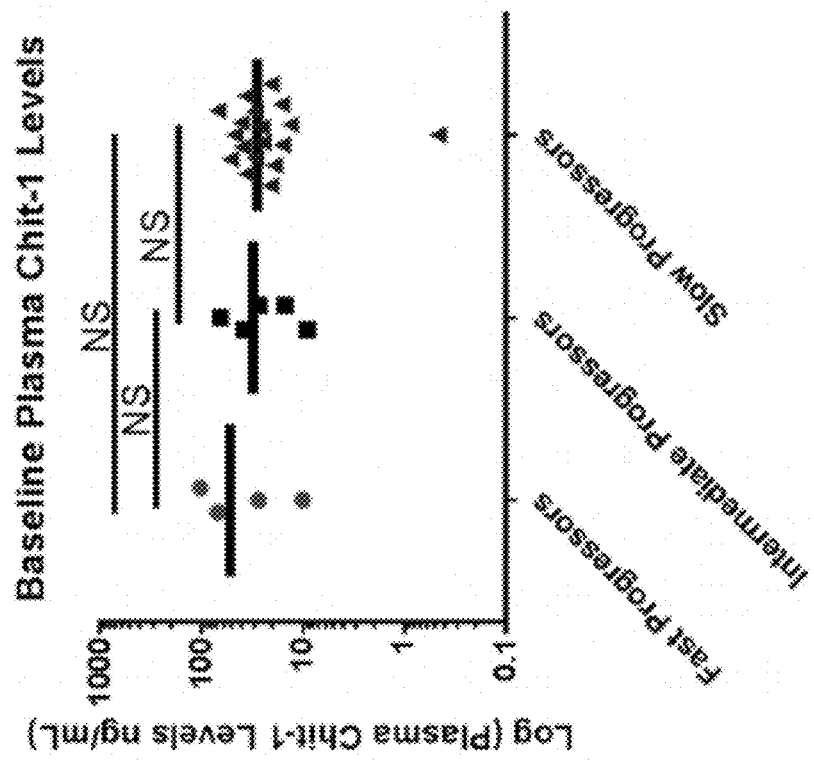
FIG. 2E. Baseline levels of plasma Chit-1 (n=4 FPs, 5 IPs, and 21 SPs). **=$p<0.01$; *=$p<0.05$; NS=not significant. p-values from linear mixed effects modeling indicate the significance level in which the slopes differ from 0 as assessed by SPSS with $p<0.05$ being considered significant.
Figure 2F:
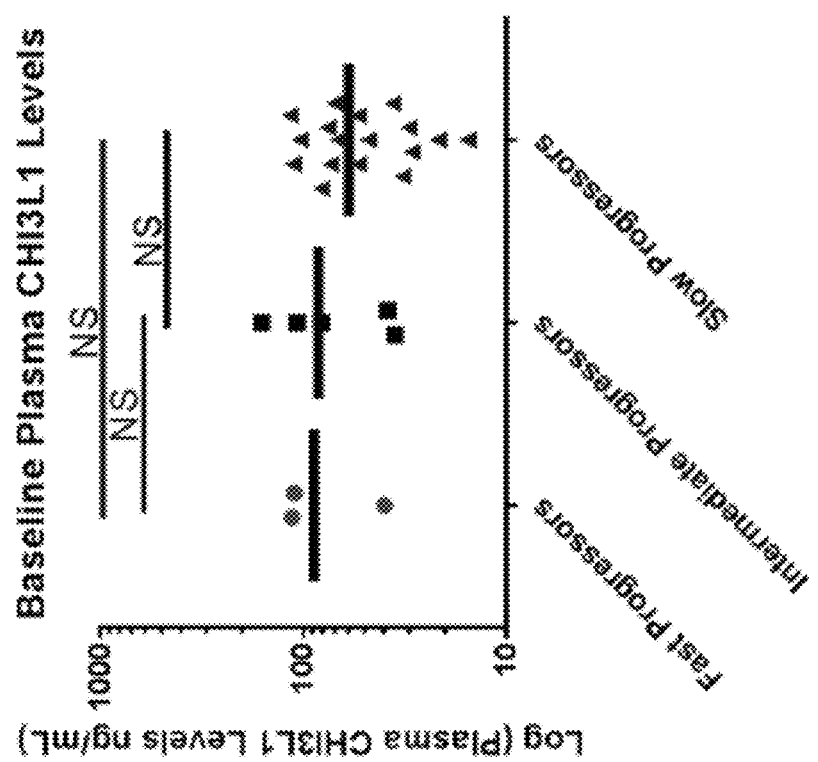
FIG. 2F. Baseline levels of plasma CHI3L1 (n=3 FPs, 5 IPs, and 17 SPs). The solid lines represent the overall linear fit of the longitudinal measurements of each chitinase in FPs (red), SPs (blue), and IPs (black). **=$p<0.01$; *=$p<0.05$; NS=not significant. p-values from linear mixed effects modeling indicate the significance level in which the slopes differ from 0 as assessed by SPSS with $p<0.05$ being considered significant.
Figure 2G:
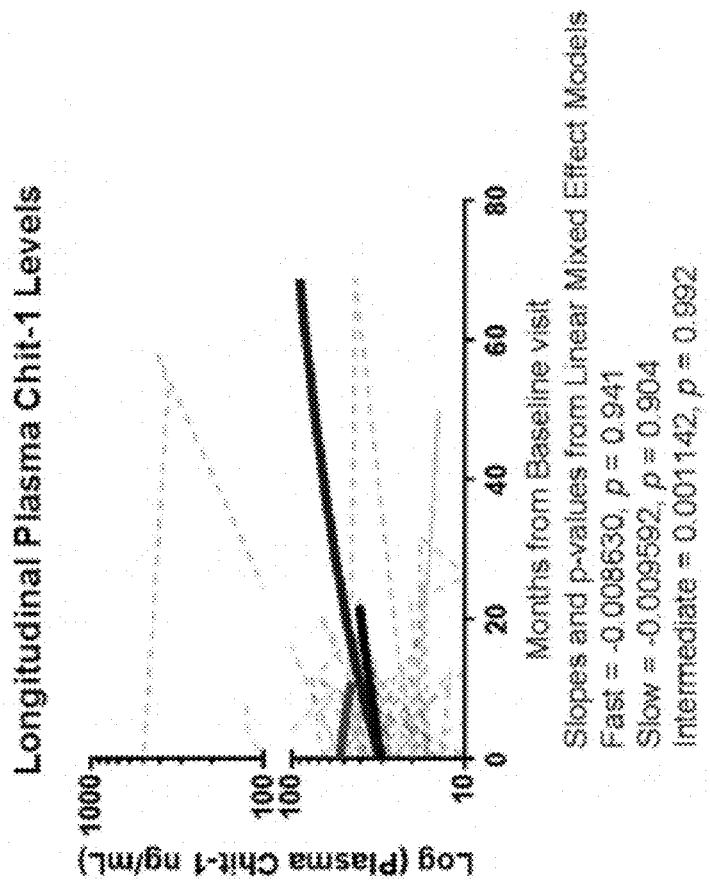
FIG. 2G. Longitudinal levels of plasma Chit-1, in which each dotted line represents an individual patient. The solid lines represent the overall linear fit of the longitudinal measurements of each chitinase in FPs (red), SPs (blue), and IPs (black). **=$p<0.01$; *=$p<0.05$; NS=not significant. p-values from linear mixed effects modeling indicate the significance level in which the slopes differ from 0 as assessed by SPSS with $p<0.05$ being considered significant.
Figure 2H:
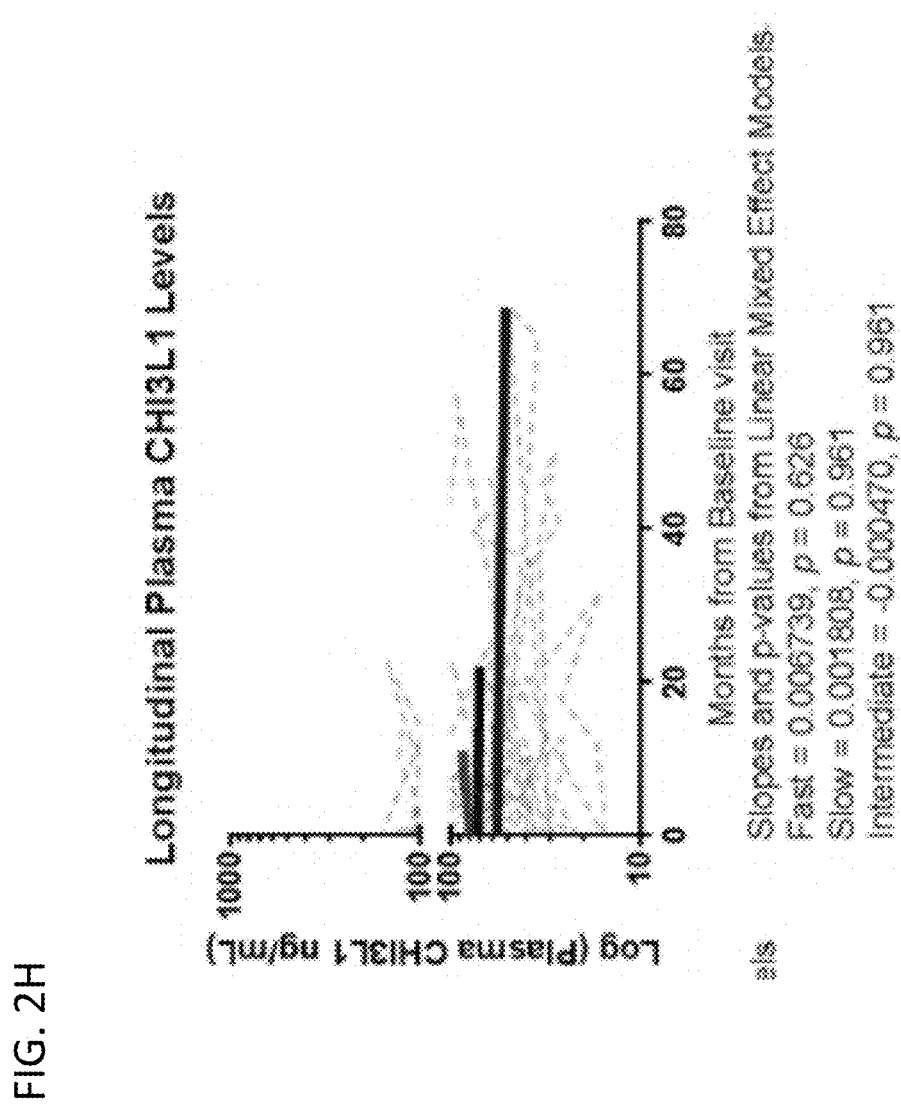
FIG. 2H. Longitudinal levels of plasma CHI3L1, in which each dotted line represents an individual patient. The solid lines represent the overall linear fit of the longitudinal measurements of each chitinase in FPs (red), SPs (blue), and IPs (black). **=$p<0.01$; *=$p<0.05$; NS=not significant. p-values from linear mixed effects modeling indicate the significance level in which the slopes differ from 0 as assessed by SPSS with $p<0.05$ being considered significant.

Levels of Chit-1 and CHI3L1 were measured in matching CSF and plasma from 42 ALS patients that had a minimum of 3 longitudinal time points (Table 1). Baseline levels of both CSF Chit-1 and CSF CHI3L1 were significantly higher in fast progressors (FP) as compared to slow progressors (SP) (FIGS. 2A and 2B). No significant difference was observed in SP vs. intermediate progressors (IP) or between FPs vs. IPs for either biomarker. To assess the rate of change of each chitinase over time, slopes from linear mixed effects modeling analyses were determined (FIGS. 2C-D). No significant rise in the slopes of CSF Chit-1 or CSF CHI3L1 was observed. Collectively, these results combined with the assessment of baseline levels suggest that, over time, CSF Chit-1 and CSF CHI3L1 remain constant but levels are significantly higher in fast FPs as compared to SPs, while no differences were observed in SPs vs. IPs or FPs vs. IPs.

TABLE 1

Patient demographics.

| | ALS | Disease controls (DCs) | Healthy Controls (HC) |
|---|---|---|---|
| Number of subjects with baseline visit | 118 | 17 | 24 |
| Number of subjects with 2 visits | 80 | 2 | 10 |
| Number of subjects with 3 visits | 42 | 0 | 1 |
| Number of subjects with 4 visits | 17 | 0 | 0 |
| Number of subjects with 5 visits | 12 | 0 | 0 |
| Gender (M/F) | 70/49 | 11/6 | 11/13 |
| Onset site (Bulbar:Limb) | 29:88 | N/A | N/A |
| Average age of onset (Mean ± SD) | 54 ± 10 | N/A | N/A |
| Average age at Baseline (Mean ± SD) | 57 ± 10 | 58 ± 11 | 53 ± 13 |
| Number of C9orf72 patients | 14 | N/A | N/A |
| Number of SOD1 patients | 1 | N/A | N/A |

No statistical differences were determined between age at baseline of ALS vs. DCs (p = 0.99), ALS vs. HCs (p = 0.74) or DCs vs. HCs (p = 0.84) as determined by the Kruskal Wallis test with a Dunn correction applied. No sex differences were observed (p = 0.41) as determined by Chi-squared test.

These trends were not observed with plasma Chit-1 or plasma CHI3L1 where no differences in baseline levels, and no changes in slopes, were detected (FIGS. 2E-H). These results indicate that no differences over time for either chitinase in plasma were observed. A similar analysis was performed using CSF and plasma pNFH levels, and no changes were observed over time in either biofluid (FIG. 9) similar to previous observations in plasma.

Figure 3A:
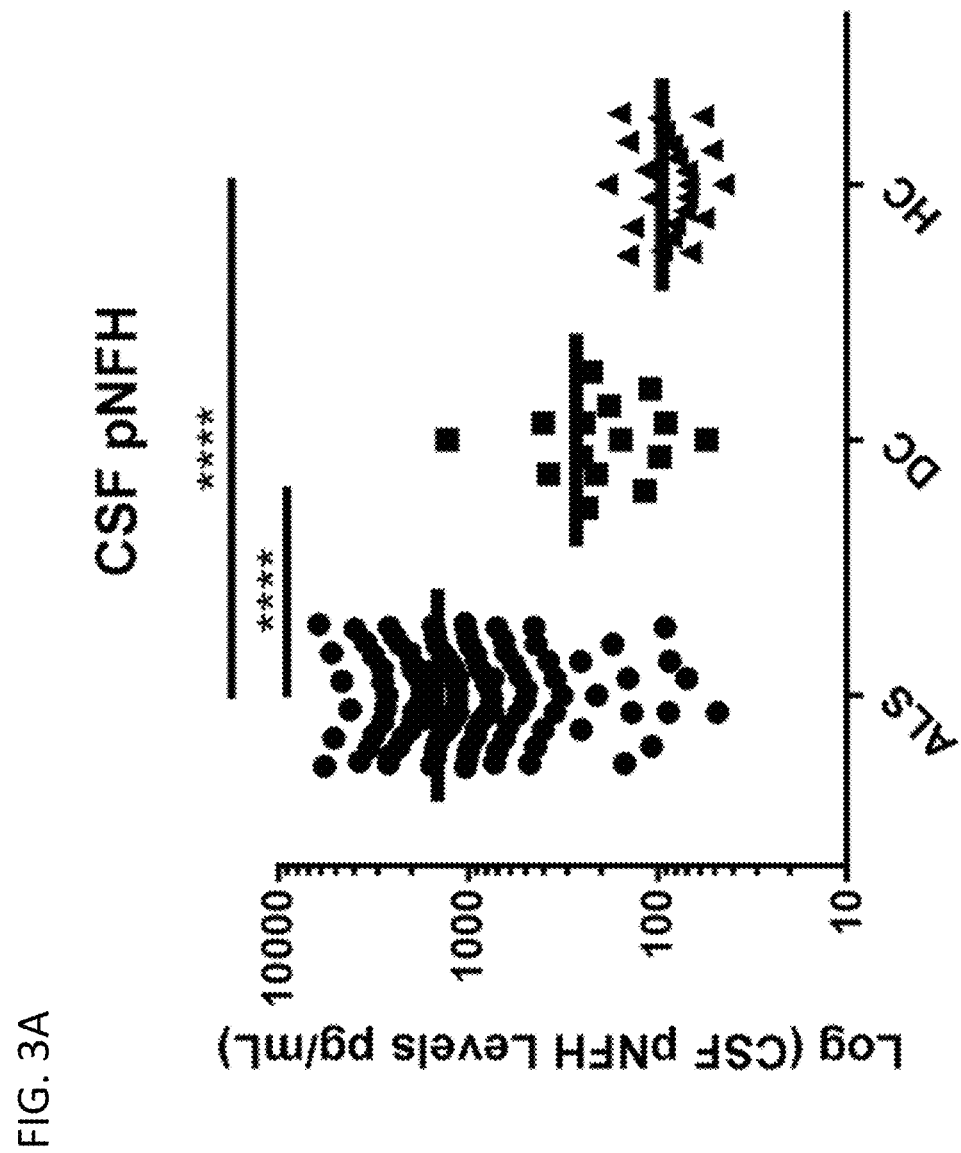
FIG. 3A. Levels of CSF pNFH at baseline visits for ALS patients, disease controls (DC), and healthy controls (HC). ****$p<0.0001$, and NS=not significant.
Figure 3B:
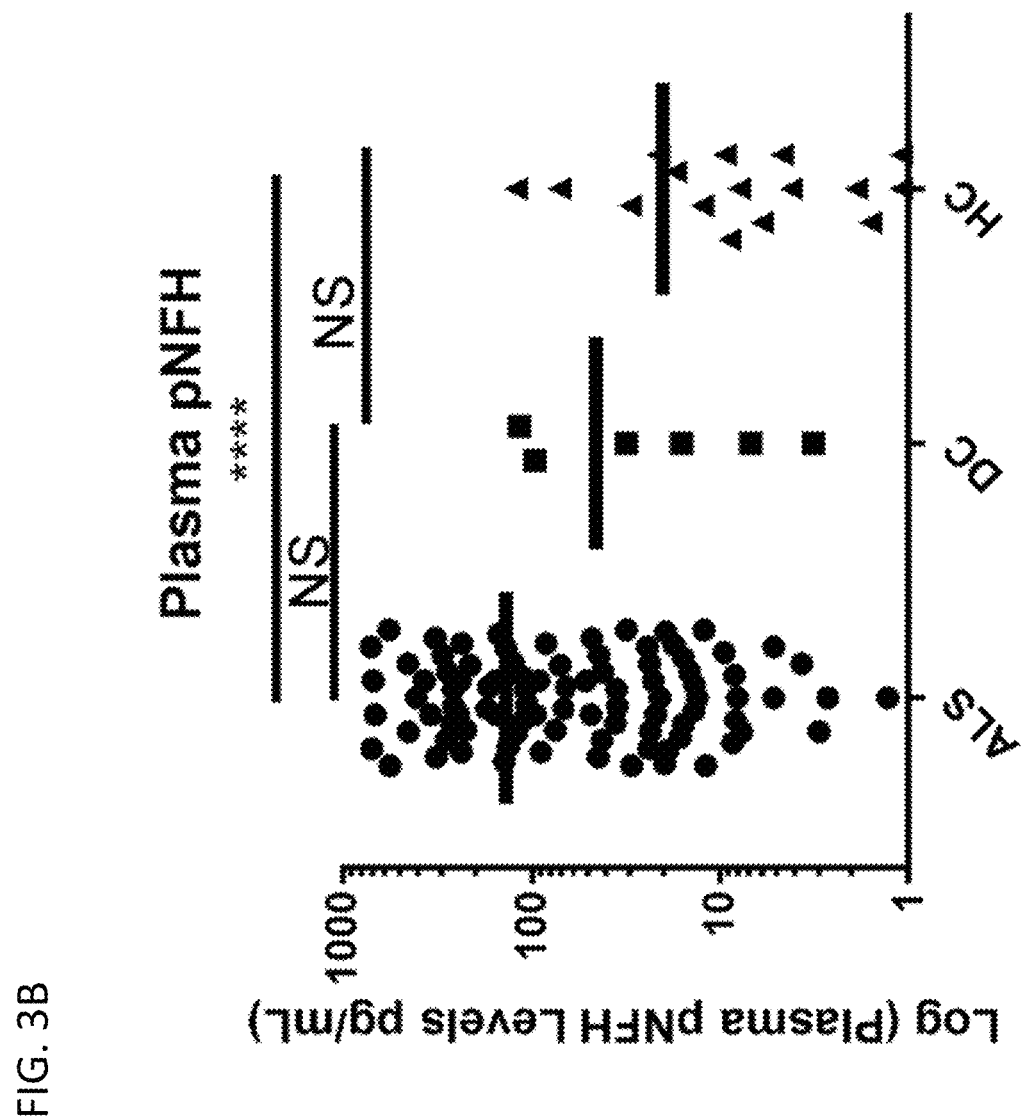
FIG. 3B. Levels of plasma pNFH at baseline visits for ALS patients, disease controls (DC), and healthy controls (HC). ****$p<0.0001$, and NS=not significant.
Figure 3C:
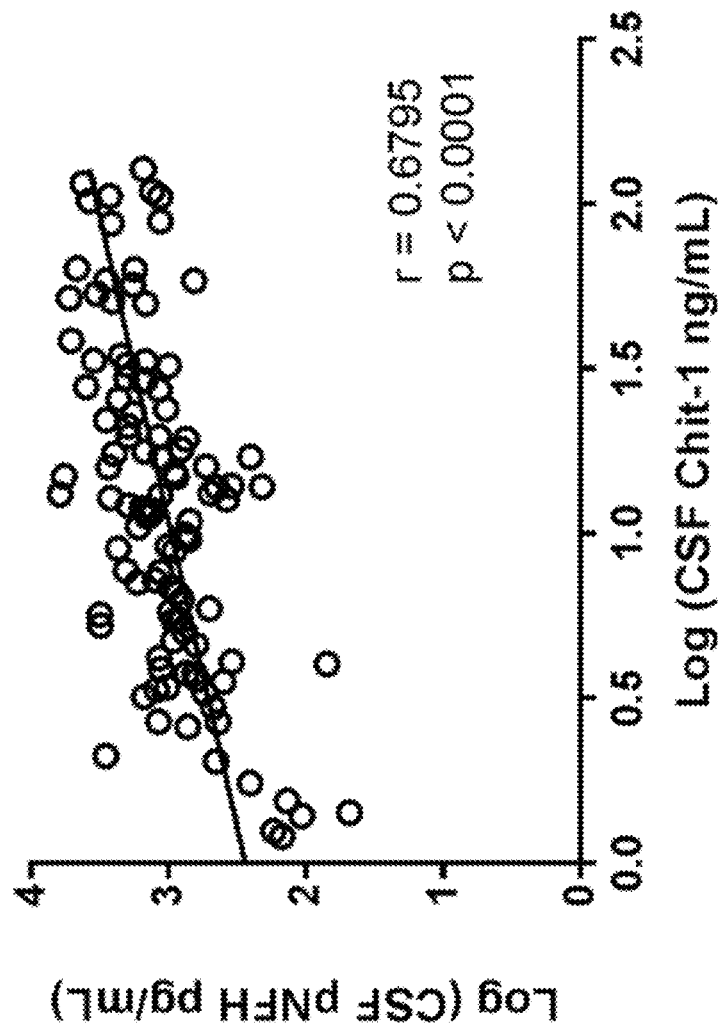
FIG. 3C. Correlation analysis between CSF Chit-1 and pNFH using data from the baseline visits in ALS patients.
Figure 3D:
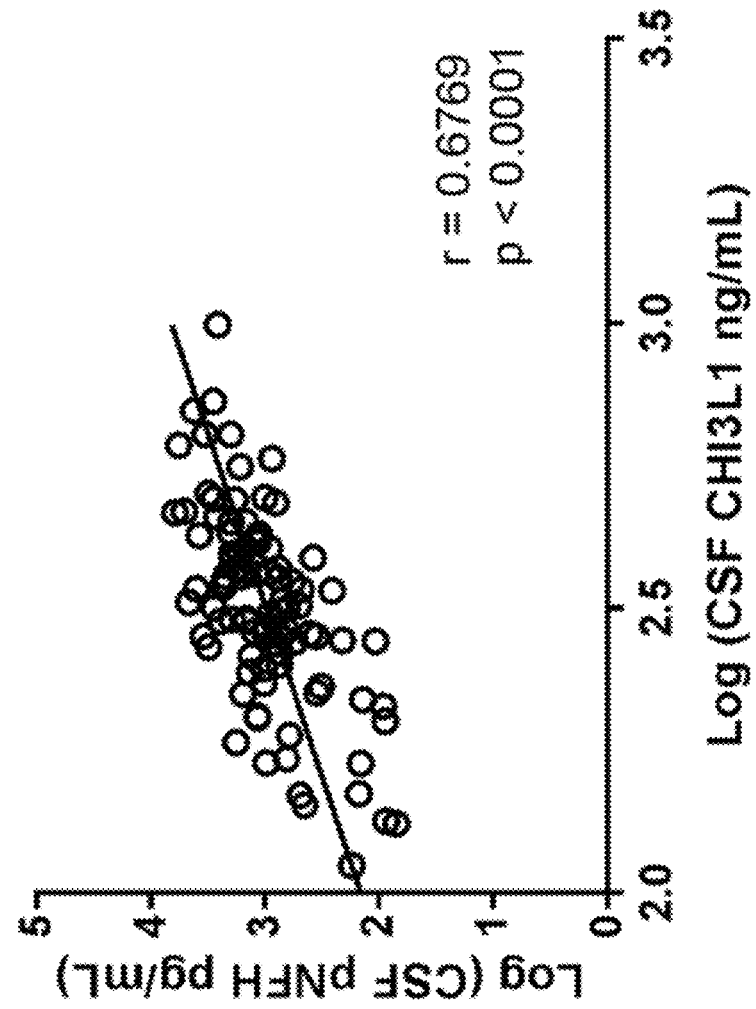
FIG. 3D. Correlation analysis between CSF CHI3L1 and CSF pNFH using data from the baseline visits in ALS patients.
Figure 10A:
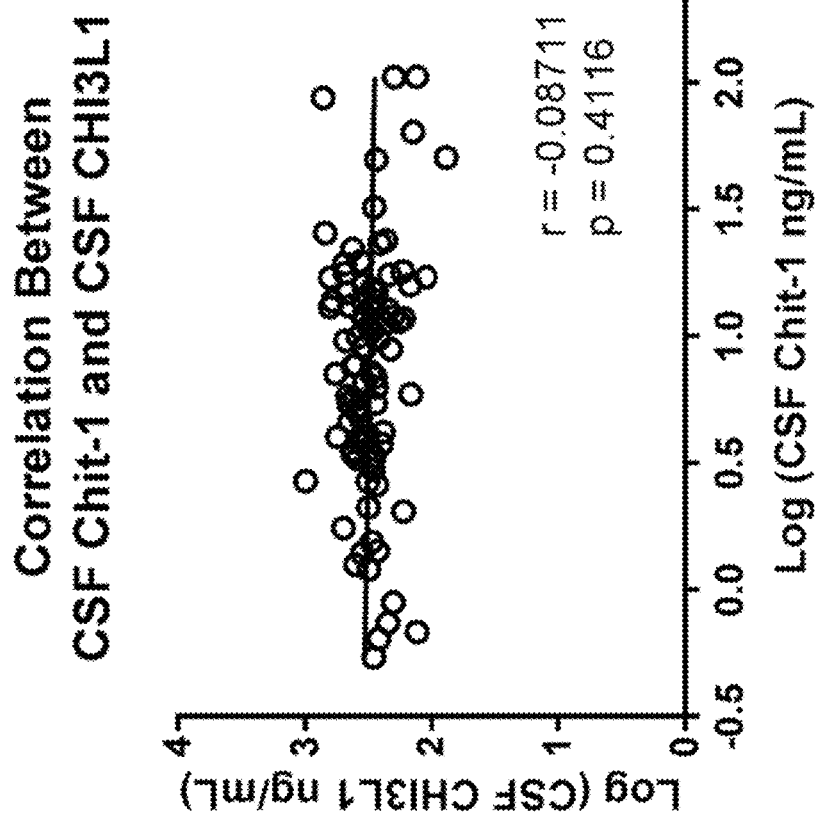
FIG. 10A. Correlation analysis between Chit-1 and CHI3L1 in CSF. Pearson's correlation coefficient (r) was used for all pair-wise analyses, with p<0.05 considered significant.
Figure 10B:
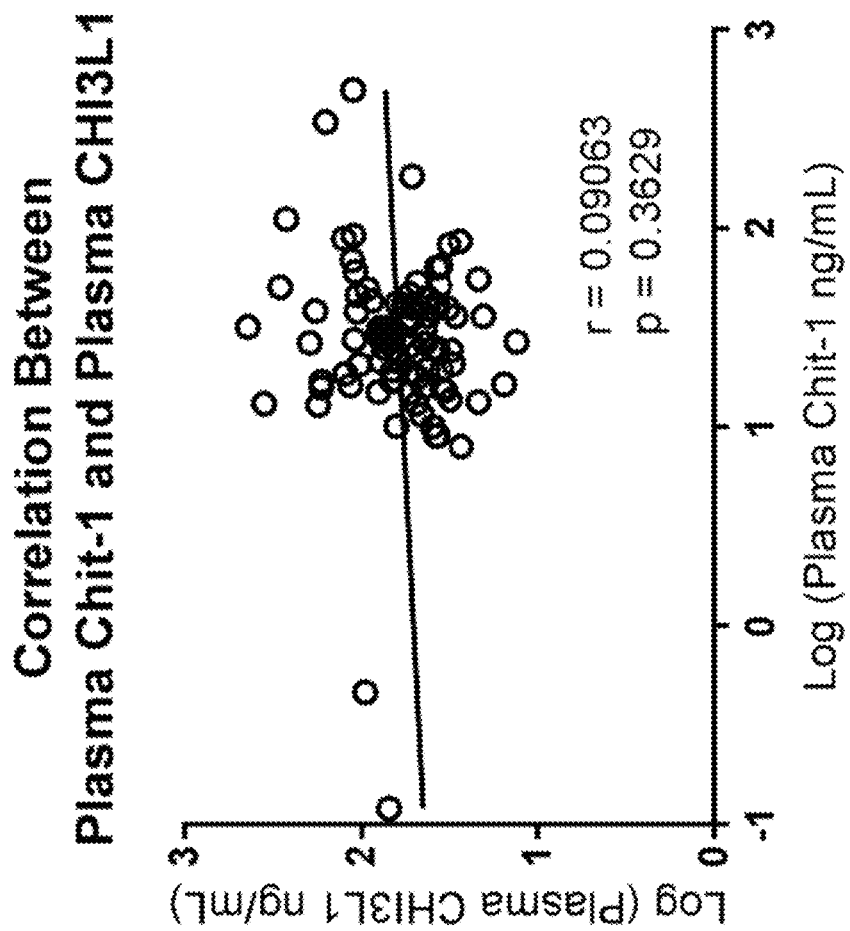
FIG. 10B. Correlation analysis between Chit-1 and CHI3L1 in plasma. Pearson's correlation coefficient (r) was used for all pair-wise analyses, with p<0.05 considered significant.

Example 4. Chitinase Levels Correlate with Phosphorylated Neurofilament Heavy Chain (pNFH) in CSF Similar to prior studies, levels of both CSF and plasma pNFH were significantly higher in ALS patients as compared to control groups (FIGS. 3A-1B). Interestingly, both CSF Chit-1 and CSF CHI3L1 correlated with CSF pNFH (FIGS. 3C-D), Chit-1 vs pNFH; r=0.6795 p<0.0001, CHI3L1 vs pNFH; r=0.6769 p<0.0001). No significant correlation between either chitinase to pNFH in plasma was detected. No significant correlation between Chit-1 and CHI3L1 was detected in either CSF or plasma (FIGS. 10A and 10B). These results suggest that specific biomarkers in white matter highlight novel ideas that glial cells expressing CHI3L1 may be protective/regenerative and not causing damage, and relevant for a large host of neurologic conditions impacting the white matter, such as multiple sclerosis and other neurodegenerative diseases.

Example 5. CHI3L1 Immunostaining in Post Mortem Tissues

Figure 4:
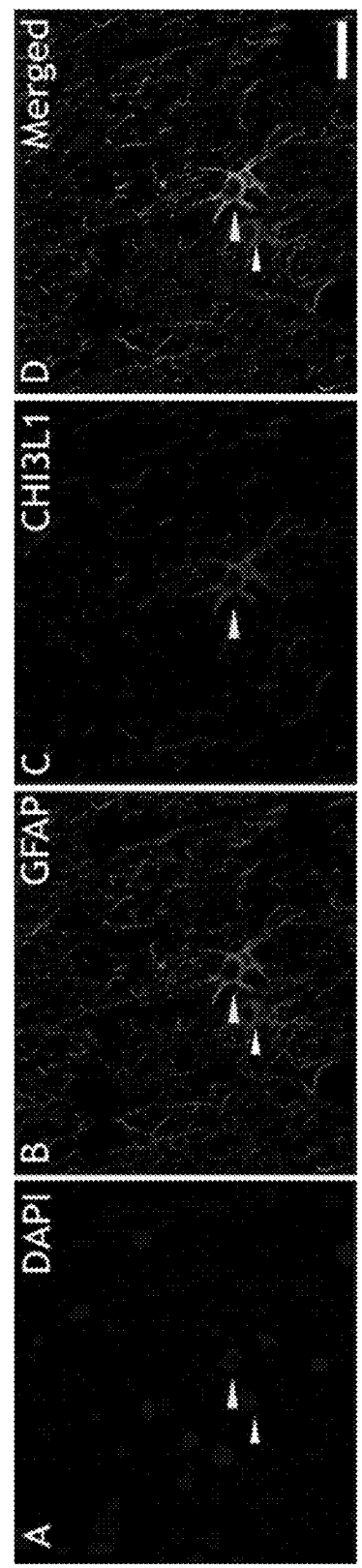
FIG. 4. CHI3L1 expression in a subset of activated astrocytes. Double-label confocal microscopy for GFAP (green) and CHI3L1 (red) in motor cortex of ALS patient, with nuclei counterstained using DAPI (blue). Panel A: DAPI; Panel B: GFAP; Panel C: CHI3L1; and Panel D: merged image. Scale bar=20 μm for all panels. White arrowhead denotes a GFAP positive astrocyte and yellow arrowhead denotes GFAP and CHI3L1 positive astrocyte.
Figure 5A:
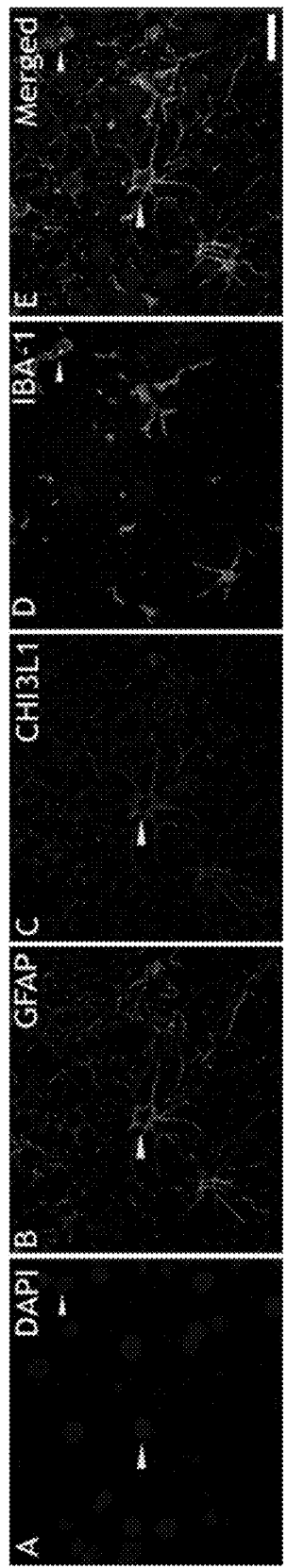
FIG. 5A. Triple-label immunofluorescence confocal microscopy of ALS motor cortex. Panel A: DAPI; Panel B: GFAP; Panel C: CHI3L1; Panel D: Iba-1; and Panel E: merged image demonstrate co-localization of CHI3L1 in a subset of GFAP positive astrocyte (yellow arrowheads) with no co-localization of CHI3L1 and Iba-1 (white arrowhead). Scale bar=20 μm for all panels.
Figure 5B:
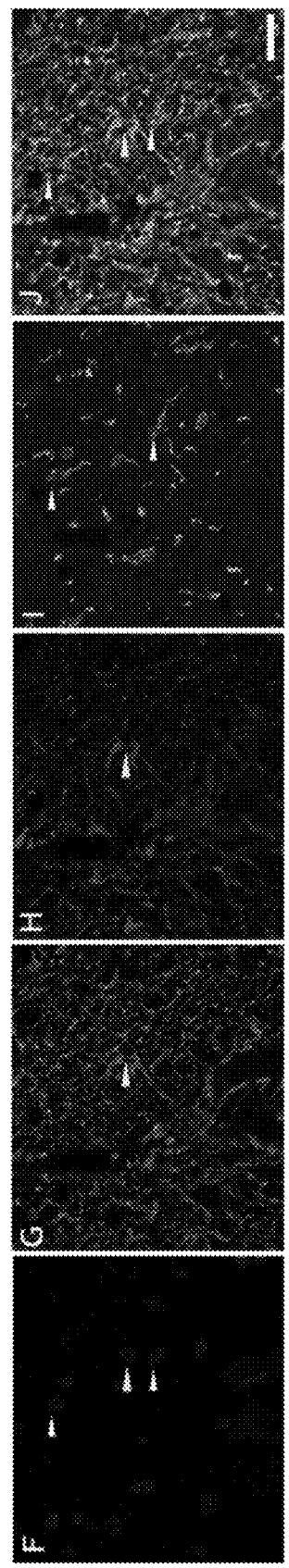
FIG. 5B. Triple-label immunofluorescence confocal microscopy of ALS lumbar spinal cord. Panel F: DAPI; Panel G: GFAP; Panel H: CHI3L1; Panel 1: Iba-1; and Panel J: merged image demonstrate co-localization of CHI3L1 in a subset of GFAP positive astrocyte (yellow arrowheads) with no co-localization of CHI3L1 and Iba-1 (white arrowhead). Scale bar=20 μm for all panels FIG. 6A. Immunohistochemistry for CHI3L1 in motor cortex gray and white matter of (Panels i and ii) ALS patients, (Panels iii and iv) neurologic disease controls, and (Panels v and vi) non-neurologic disease controls using a 4× objective. Dashed lines show the gray and white matter interface. Scale bar=100 μm.
Figure 6A:
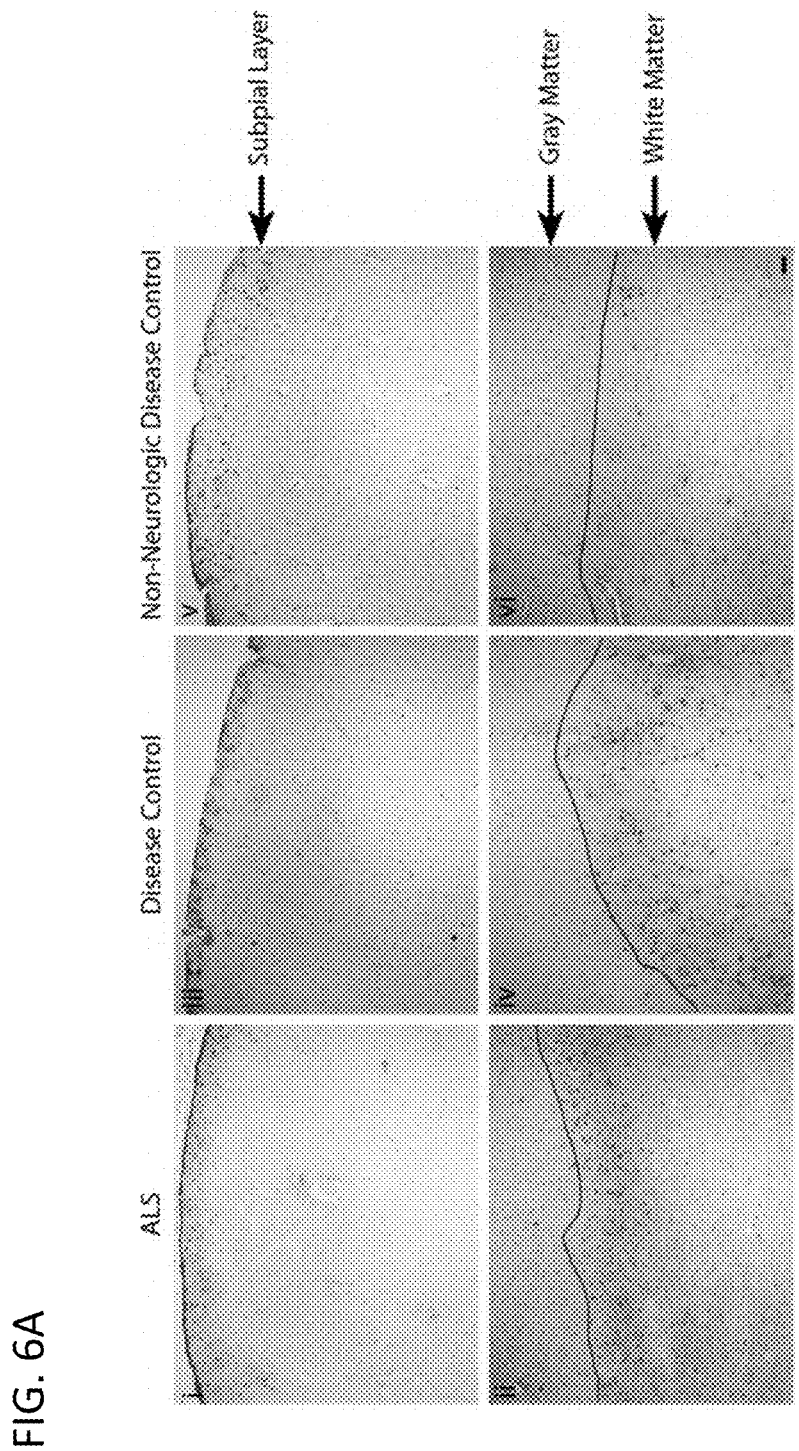
FIG. 6B. Representative images used for quantification of CHI3L1 positive cells in (Panel i) ALS, (Panel ii) neurologic disease controls, and (Panel iii) non-neurologic disease controls using a 10× objective. Scale bar=40 μm.
FIG. 6C. Quantification for the number of CHI3L1 positive cells in at least 5 fields of view of white matter (Area=633.1 $mm^2$) for each case. Data analysis was performed in a blinded manner (n=12 ALS, 3 neurologic disease controls, 4 Non-Neurologic Disease Controls). *$p<0.05$.
Figure 6B:
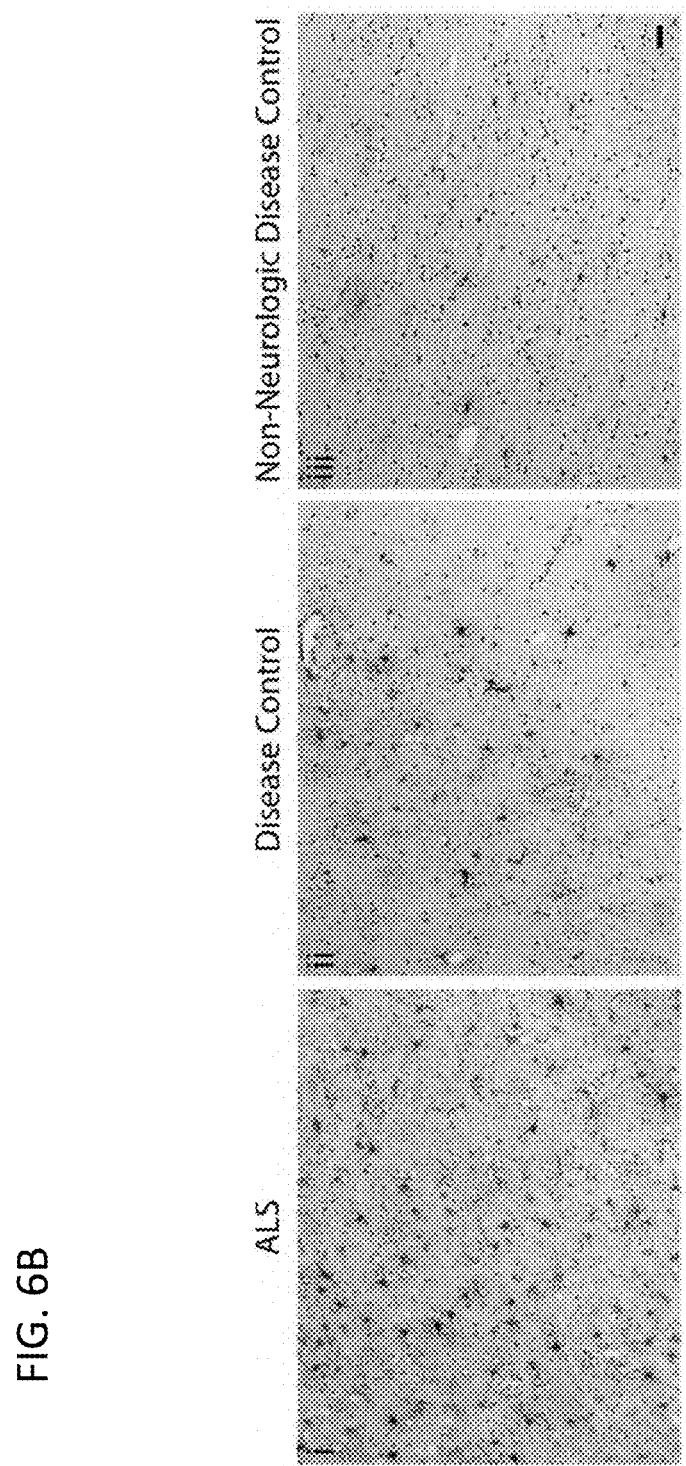
Figure 6C:
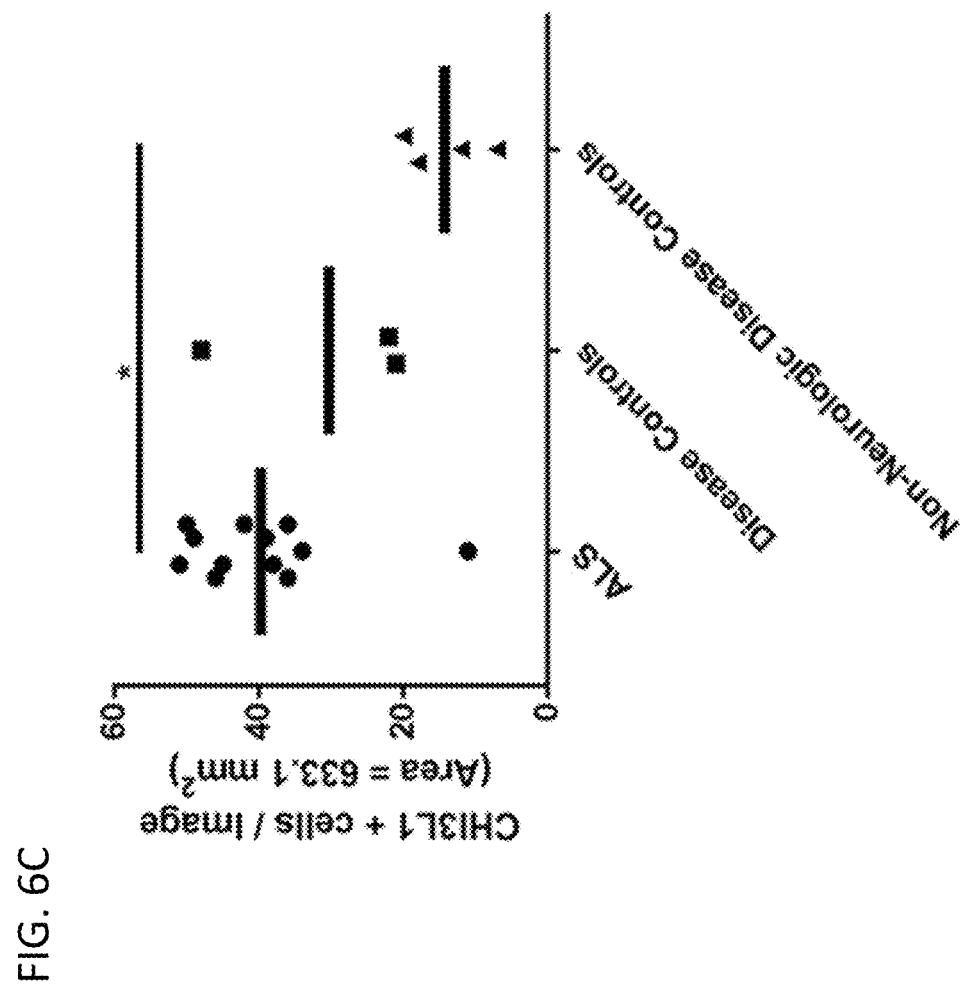
Figure 11A:
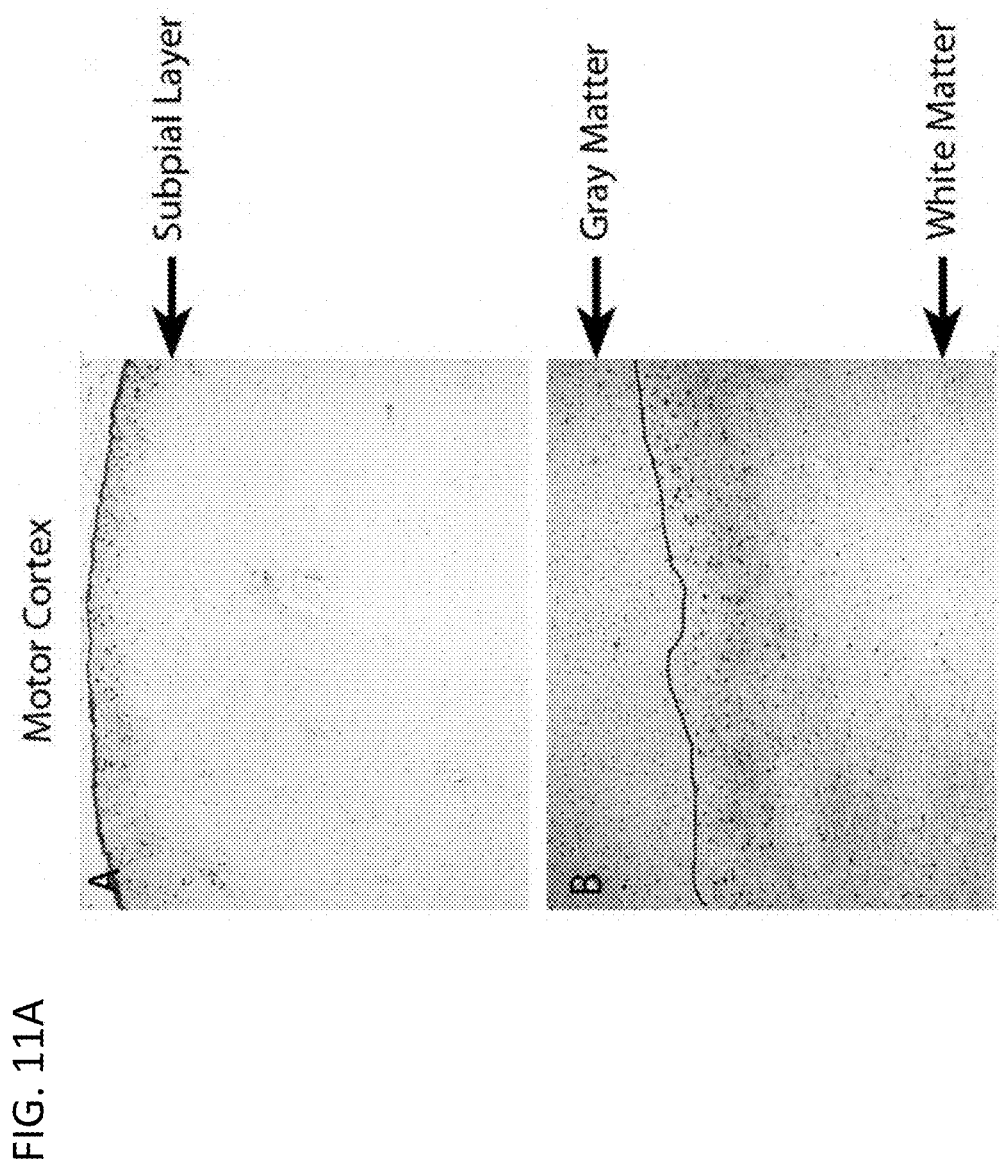
FIG. 11A. Immunohistochemistry for CHI3L1 in motor cortex (Panels A and B), of ALS patients. CHI3L1 is detected predominantly in subpial layers and white matter. Dashed lines show the gray and white matter interface in panel B. Small numbers of CHI3L1 positive astrocytes are detected in the deep gray matter and predominately around blood vessels. Scale bar=100 µm. Dashed lines show the gray and white matter interface.
Figure 11B:
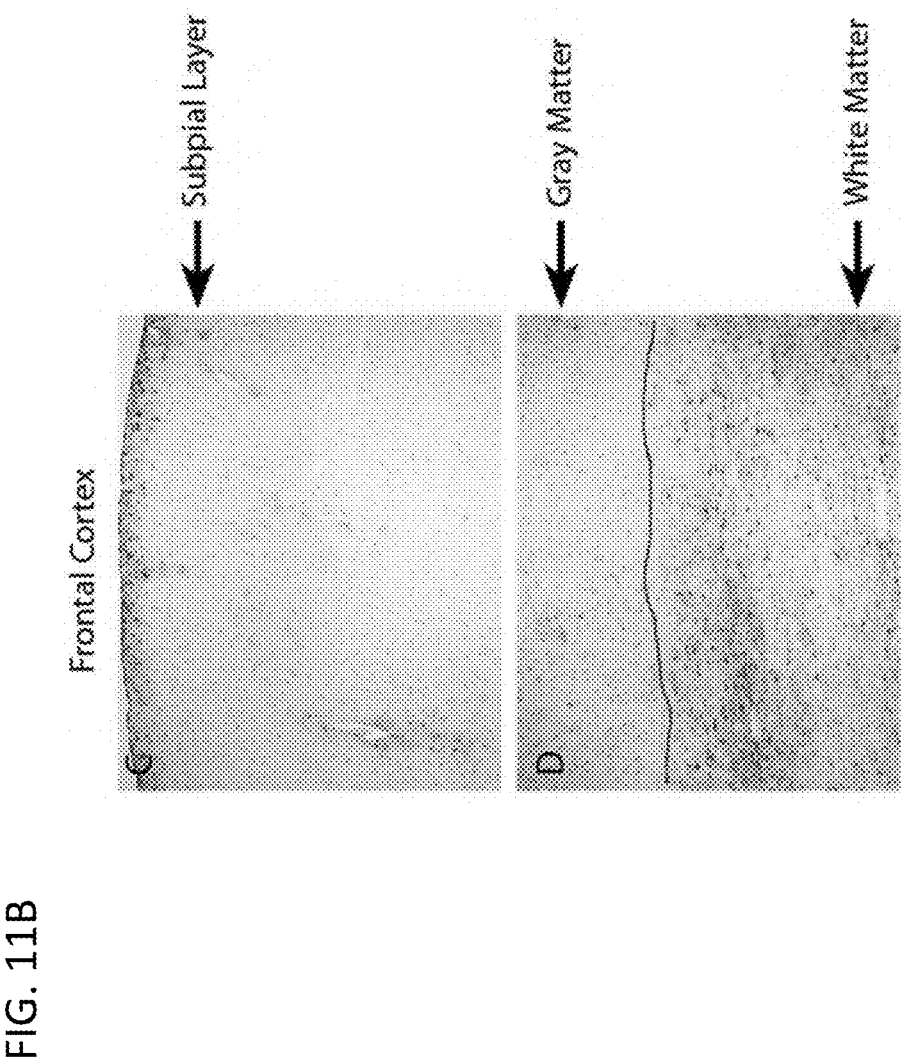
FIG. 11B. Immunohistochemistry for CHI3L1 in frontal cortex (Panels C and D) of ALS patients. CHI3L1 is detected predominantly in subpial layers and white matter. Dashed lines show the gray and white matter interface in panel D. Small numbers of CHI3L1 positive astrocytes are detected in the deep gray matter and predominately around blood vessels. Scale bar=100 µm. Dashed lines show the gray and white matter interface.
Figure 11C:
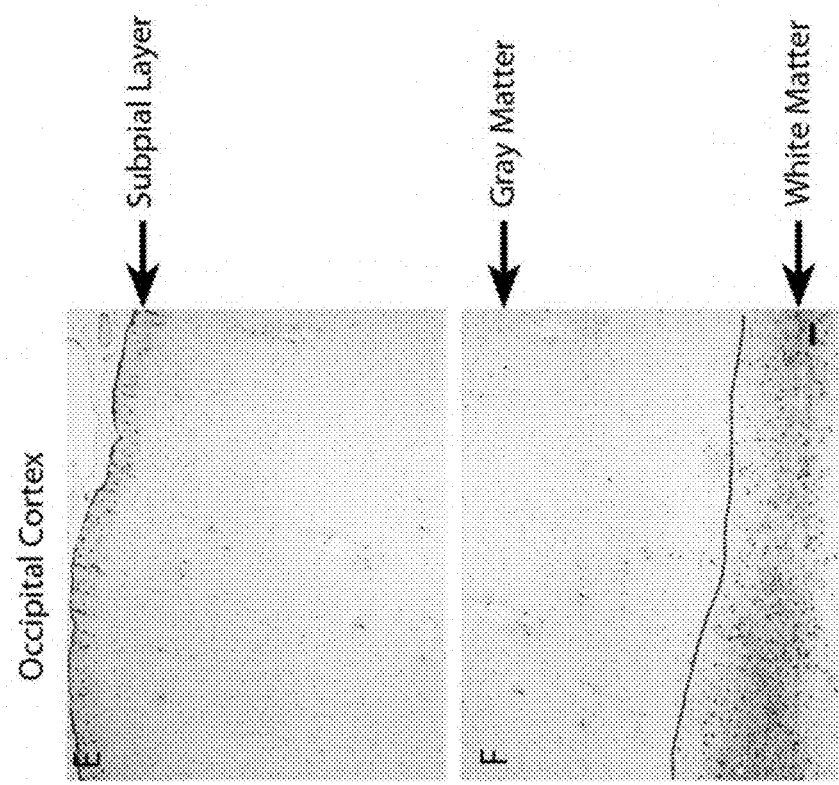
FIG. 11C. Immunohistochemistry for CHI3L1 in occipital cortex (Panels E and F) of ALS patients. CHI3L1 is detected predominantly in subpial layers and white matter. Dashed lines show the gray and white matter interface in panel F. Small numbers of CHI3L1 positive astrocytes are detected in the deep gray matter and predominately around blood vessels. Scale bar=100 µm. Dashed lines show the gray and white matter interface.

A prior study demonstrated Chit-1 co-localization with Iba-1-expressing microglia in ALS spinal cord. To determine cell type specific expression of CHI3L1 in ALS, double label immunofluorescence confocal microscopy was performed in motor cortex tissue sections (FIG. 4, panels A-D). Co-localization of GFAP and CHI3L1 confirmed that CHI3L1 positive cells are activated astrocytes (FIG. 4, panel D, yellow arrowhead). Interestingly, not all GFAP positive astrocytes exhibited CHI3L1 expression (FIG. 4, panel D, white arrowhead). Triple label confocal microscopy demonstrated that CHI3L1 positive cells were GFAP positive and Iba-1 negative in the white matter of both motor cortex (FIG. 5A, Panels A-E) and lumbar spinal cord (FIG. 5B, Panels F-J), indicating that CHI3L1 is a specific biomarker for a subset of activated astrocytes in the white matter of ALS patients. To further assess differences in the amount and distribution of CHI3L1 positive cells in ALS and controls, immunohistochemistry (IHC) for CHI3L1 in the motor cortex of ALS, DCs, and NNDCs was performed. It was observed that CHI3L1 positive cells predominately in the subpial region and white matter (FIG. 6A). Interestingly, a similar staining pattern was observed in the frontal and occipital cortex of ALS cases (FIG. 11). Next, CHI3L1 positive cells in both the gray and white matter of the motor cortex were quantified. In the gray matter, no significant differences between ALS, DCs and NNDCs were observed. However, in the white matter, approximately a 2.8 fold increase of CHI3L1 positive cells in ALS white matter as compared to NNDCs was observed (FIGS. 6B-C). No significant differences were observed in the white matter between ALS and DCs or between DCs and NNDCs.

Discussion for Examples 1-5

Recent findings that CSF Chit-1 is significantly higher in ALS samples as compared to both DCs and HCs were confirmed in the examples described herein using unbiased proteomic or targeted immunoassay methods. CSF CHI3L1 was also higher in ALS as compared to HCs, confirming results from some studies but contrasting with others. It was further determined that CSF CHI3L1 was higher in DCs as compared to HCs supporting a role for this protein as a candidate biomarker for multiple neurologic diseases, including multiple sclerosis and Alzheimer's Disease. Plasma levels of both Chit-1 and CHI3L1 showed no significant difference between ALS and control groups. Similar observations were recently reported in serum of ALS patients. Although several outliers with high levels of plasma Chit-1 or CHI3L1 were observed in the ALS group, ALS patients with high plasma Chit-1 did not exhibit high levels of CHI3L1. Based on ROC analysis, it was demonstrated that a combination of Chit-1 plus CHI3L1 outperforms either chitinase alone in plasma but not CSF in classifying ALS vs. controls. However, CSF Chit-1 alone can also classify ALS vs. controls.

Elevated levels of Chit-1 and CHI3L1 in the CSF are indicative of glial activation that may potentiate neuroinflammation and motor neuron death in ALS. Prior studies demonstrated increased astrocyte infiltration in the spinal cord of SOD1 transgenic mice, and the presence of CHI3L1 positive cells in lumbar spinal cord of ALS patients. Positron emission tomography (PET) demonstrated increased numbers of activated microglia in the motor cortex and corticospinal tract in ALS patients. A recent study identified increased Chit-1 immunoreactivity in activated microglia in the spinal cord white matter of ALS patients. Data are lacking on the cell type expression of CHI3L1 in ALS. In the studies described above, an ~2.8 fold increase in CHI3L1 positive cells in the white matter of motor cortex of ALS patients as compared to NNDCs was identified. CHI3L1 positive cells were also evident in subpial layers, but only scattered positive cells were observed in the deeper layers of the gray matter. Similar results have also shown an increase in GFAP containing astrocytes in the white matter of ALS frontal cortex as compared to controls. Confocal microscopy was used to demonstrate that CHI3L1 is expressed by a subset of activated astrocytes, but not microglia located in the white matter of the motor cortex and spinal cord of ALS patients (FIGS. 4 and 5). While the consequence of increased CHI3L1 expressing astrocytes in the white matter of ALS patients is unclear, it is proposed that increased CHI3L1 expressing astrocytes directly contribute to axonal degeneration in the white matter. This is supported by the correlation observed in the studies above between CSF CHI3L1 and CSF pNFH (a marker of axonal injury). Other studies have proposed a link between activated white matter astrocytes and myelin degeneration, and a role for chitinases in modulating the extracellular matrix. Therefore, our results suggest that increased levels of CHI3L1 in the white matter may disrupt normal oligodendrocyte function or act on extracellular matrix proteins to modulate axonal damage and further exacerbate neuroinflammation. Interestingly, only a subset of GFAP positive astrocytes co-localized with CHI3L1, suggesting the presence of different astrocytic subtypes in the gray and white matter. Additionally, while CHI3L1 is expressed by activated astrocytes and not microglia in the frontal cortex of AD patients, CHI3L1 expression was detected in both astrocytes and microglia in MS. Together, our results highlight a disease-specific expression pattern for chitinase proteins.

To assess longitudinal changes in protein levels, the baseline levels and the rate of change of each chitinase over time was determined. It was demonstrated that, over time, both CSF Chit-1 and CSF CHI3L1 remain relatively constant but segregate ALS patients based on rate of disease progression. While CSF chitinase levels distinguish between FP and SP forms of ALS, plasma chitinase levels showed no significant differences over time, and did not distinguish FP from SP ALS patients. Similar trends were observed using serum from FP and SP ALS patients. Our data suggest the potential utility of CSF chitinases for segregation of ALS patients based on disease progression rate, though these results must be validated in future studies.

Overall, the studies described in Examples 1-5 above highlight that CSF rather than plasma chitinases are candidate ALS biomarkers, and levels correlate with rate of disease progression as measured by change in ALSFRS-r over time. Furthermore, CHI3L1 expression occurs in a subset of activated astrocytes predominately in the white matter of ALS patients.

Methods for Examples 1-5

Biofluid Sample Description

CSF and matching plasma from ALS patients, neurologic disease controls (DCs), and healthy controls (HCs) were obtained from the Northeast ALS Consortium (NEALS) Biofluid Repository and the Mayo Clinic Biorepository. All subjects provided IRB approved informed consent at either the Mayo Clinic or the site of participant enrollment for samples collected by the NEALS biorepository. All ALS subjects were defined by El Escorial criteria by experienced and licensed neurologists. CSF and plasma was collected from 118 ALS patients and 41 controls (Table 1).

The DC group (n=17) was comprised of patients with a range of diseases including brain metastases, viral encephalitis, neuropathy, multiple sclerosis, upper motor neuron disease, primary lateral sclerosis, chronic inflammatory demyelinating polyneuropathy, idiopathic sensorimotor polyneuropathy, spinocerebellar ataxia, lymphoma, and lower motor neuron disease. The 24 HCs lacked any identified neurologic deficits. CSF and plasma samples were collected from these individuals using methods as previously described. Longitudinal samples collected at clinic visits that were separated by at least three months were obtained and the numbers of subjects providing longitudinal samples are shown in Table 1. Tissue sections from 12 ALS, 3 DCs and 4 non-neurologic diseased controls (NNDCs) were obtained from the Barrow Neurological Institute and Target ALS post mortem tissue bank cores (subject demographics listed in Table 2). Participants in the post mortem tissue bank cores provided IRB approved informed consent for the collection of post mortem tissues.

TABLE 2

Demographics of the cases used for the immunohistochemical and immunofluorescent staining.

| Case | Sex | Age at Death | Age at onset | Site of Onset | Diagnosis | C9 (+or−) |
|---|---|---|---|---|---|---|
| ALS 1 | Female | 61 | 58 | Limb | ALS | − |
| ALS 2 | Female | 63 | 61 | Limb | ALS | − |
| ALS 3 | Male | 74 | 70 | N/A | ALS | − |
| ALS 4 | Male | 74 | N/A | N/A | ALS | − |
| ALS 5 | Male | 83 | 81 | N/A | ALS | − |
| ALS 6 | Female | 51 | 47 | Bulbar | ALS | + |
| ALS 7 | Male | 44 | 40 | Limb | ALS, CTE | − |
| ALS 8 | Female | 68 | 60 | Limb | ALS, Scoliosis | − |
| ALS 9 | Female | 60 | 57 | Limb | ALS | − |
| ALS 10 | Male | 39 | 35 | N/A | ALS | − |
| ALS 11 | Female | 63 | 60 | N/A | ALS | − |
| ALS 12 | Male | 72 | N/A | N/A | ALS, FTLD | Not tested |
| DC 1 | Male | 81 | N/A | N/A | AD | − |
| DC 2 | Male | 45 | N/A | N/A | MSA | − |
| DC 3 | Male | 71 | N/A | N/A | AD | − |
| NNDC 1 | Female | 74 | N/A | N/A | Non-Neurologic Disease Control | − |
| NNDC 2 | Male | 22 | N/A | N/A | Non-Neurologic Disease Control | − |
| NNDC 3 | Female | 70 | N/A | N/A | Non-Neurologic Disease Control | − |
| NNDC 4 | Female | 92 | N/A | N/A | Non-Neurologic Disease Control | − |

N/A indicates that this information was not documented.
CTE-Chronic Traumatic Encephalopathy, FTLD-Frontotemporal Lobar Degeneration AD-Alzheimer's Disease, MSA-Multiple System Atrophy Chitinase and pNFH Measurements A sandwich enzyme linked immunosorbent assay (ELISA) was used to quantify Chit-1 in CSF and matching plasma samples. 96 well plates consisting of ImmunoClear standard module well strips for ELISAs (Thermo Fisher, Waltham, MA) were coated with goat anti-human Chit-1 (R&D systems Minneapolis, MN) over night at 4° C., washed and blocked. Purified recombinant Chit-1 protein (R&D systems) was diluted in 1× TBS (20 mM Tris, 150 mM sodium chloride, 0.05% ProClin 300, 1% BSA, pH=7.6) to generate a standard curve from 0-10 ng/mL. CSF or plasma samples were also diluted in 1× TBS. For ALS samples, a dilution of 1:20 was used for CSF and 1:100 was used for plasma. For control samples a dilution of 1:20 was used for both CSF and plasma. Standards and samples were added to individual plate wells and incubated at room temperature for 90 min. Mouse anti-human Chit-1 (R&D systems) and goat anti-mouse IgG—HRP (Promega, Madison, WI) were used for detection. The peroxidase reaction was developed using 3,3',5,5'-Tetramethylbenzidine (TMB; Sigma Aldrich, St. Louis, MO) and stopped using 1 N hydrochloric acid (HCl). For the Chit-1 assay, average intra-assay and inter-assay coefficient of variation (CV) were below 15% for both CSF and plasma. Lower limit of quantification was 21.4 pg/mL for CSF and 20.3 pg/mL for plasma. Spike in recovery assays produced recoveries of 96% for CSF and 93% for plasma. Linearity test produced a regression coefficient ($R^2$) greater than 0.99 for both CSF and plasma. For CHI3L1, a human CHI3L1 DuoSet ELISA kit (R&D systems) was used following manufacturer instructions. For both ALS and control samples, a dilution of 1:400 was used for CSF and 1:100 for plasma. Assay performance characteristics for the commercial CHI3L1 immunoassay are available in the manufacturer's insert. All samples and standards were run in duplicate on each plate.

The Meso Scale Discovery immunoassay was employed to measure pNFH as previously described. CSF samples were diluted 1:8 in 1× TBS while plasma was diluted 1:4 in 1× TBS containing 30 mg/mL urea prior to measurement.

Immunostaining and Analysis of Human Tissue

Immunohistochemistry (IHC) was performed on paraffin embedded motor cortex tissue from ALS, DCs, and NNDCs (See Table 2 for demographics). Tissue sections were de-paraffinized, rehydrated, and antigen retrieval was performed using a Target retrieval solution, pH 9 (Dako, Santa Clara, CA). Tissues were blocked using Super Block (Scytek, Logan, UT) supplemented with Avidin (Vector Labs, Burlingame, CA). Tissue sections were incubated with rabbit anti-CHI3L1 antibody (Thermo Fisher) diluted in superblock supplemented with biotin (Vector Labs) overnight. An anti-rabbit biotinylated IgG secondary antibody (Vector Labs) was subsequently added and incubated for 1 hour at room temperature. Tissues were washed in PBS and immunostaining was visualized using the Vectastain Elite ABC reagent (Vector Labs) and Vector ImmPACT Nova-RED peroxidase substrate kit (Vector Labs). Slides were counterstained with hematoxylin (Sigma Aldrich). Images were acquired using an Olympus BX40 microscope. Images were de-identified and analyzed in a blinded fashion using Image J to quantify the number of CHI3L1 positive cells with 5 images per condition and subject. Immunofluorescent (IF) staining was performed as previously described. 4',6-diamidino-2-phenylindole (DAPI) was used to stain nuclei. Autofluorescence eliminator reagent (Sigma Aldrich) was used to limit autofluorescence. IF images were acquired using a Zeiss LSM 710 confocal microscope (Zeiss, Thornwood, NY) with a 63X oil objective. Details of antibodies used for IHC and IF are shown in Table 3.

TABLE 3

Antibodies and dilutions used for the immunohistochemical (IHC) and immunofluorescent (IF) staining of post mortem tissue.

| Antibody | Species | Dilution | Company | Catalog number |
|---|---|---|---|---|
| Anti-CHI3L1 | Rabbit polyclonal | 1:100 (IF) and 1:300 (IHC) | ThermoFisher Scientific | PA5-43746 |
| Anti-Glial Fibrillary Acidic Protein antibody | Mouse Monoclonal | 1:400 (IF) | Millipore Sigma | G6171 |
| Anti-IBA-1 | Goat polyclonal | 1:250 (IF) | Abcam | Ab5076 |
| Goat anti-Mouse Alexafluor 488 | Anti-mouse | 1:200 (IF) | ThermoFisher Scientific | A-11001 |
| Goat anti-Rabbit Alexafluor 594 | Anti-Rabbit | 1:200 (IF) | ThermoFisher Scientific | A-11037 |
| Donkey anti-goat Alexafluor 546 | Anti-goat | 1:200 (IF) | ThermoFisher Scientific | A-11056 |
| Goat anti-Rabbit Alexafluor 633 | Anti-Rabbit | 1:200 (IF) | ThermoFisher Scientific | A-21070 |
| Biotinylated Goat anti-Rabbit IgG | Anti-Rabbit | 1:200 (IHC) | Vector Labs | BA-1000 |

Statistical Analyses

Statistical analysis was performed using GraphPad Prism 7.0. Cross sectional analyses were performed using the baseline visit from both ALS and control groups. All CSF and plasma measurements were log transformed prior to analysis. Kruskal-Wallis tests were performed with a post hoc Dunn correction to assess statistical differences for each biomarker with a $p<0.05$ considered significant unless specified otherwise. Correlations were analyzed using the non-parametric two tailed Pearson's correlation with a significance level set at 0.05. Receiver operator characteristic (ROC) curve was used to determine how Chit-1 and CHI3L1 were able to distinguish between ALS and control groups (both DCs and HCs) based on the area under the curve (AUC). Comparison of ROC curves was performed as previously described. Optimal cutoffs concentrations for each biomarker were selected based on the highest Youden's index. A combination of biomarkers was calculated by the summation of center and scaled concentration values. For the longitudinal analyses patients were segregated into fast, slow, and intermediate progressors using the disease progression rate which is defined by the change in ALS functional rating scale revised (ALSFRS-r) between the last and baseline visits/the amount of months between the visits. Fast progressors (FPs) were defined as those that had a disease progression rate 1 unit/month, slow progressors (SPs) had a disease progression rate <0.5 units/month, and intermediate progressors (IPs) had a disease progression rate≥0.5 units/month but less than 1 unit/month. Random slope and random intercept linear mixed effect modeling was performed using SPSS (Version 26, IBM, New York, USA) to evaluate the rate of change of each chitinase in FPs, SPs, and IPs. To further assess differences between FPs, SPs, and IPs, the baseline concentrations of Chit-1 and CHI3L1 were also compared using a Kruskal-Wallis test with p<0.05 considered significant after Dunn correction.

What is claimed is:

1. A method of categorizing a human subject for treatment, wherein the subject is suspected of having or is at risk of having amyotrophic lateral sclerosis (ALS), the method comprising:
   a) determining a CHI3L1 protein optimal cutoff concentration and a Chit-1 protein optimal cutoff concentration for categorizing a subject as having ALS, wherein determining the CHI3L1 optimal cutoff concentration and the Chit-1 optimal cutoff concentration comprises:
      (i) obtaining CHI3L1 and Chit-1 protein concentrations measured in cerebrospinal fluid (CSF) samples obtained from subjects having ALS and CSF samples from control subjects;
      (ii) obtaining a first receiver operating characteristic (ROC) curve using the CHI3L1 protein concentrations of (i) and a second ROC curve using the Chit-1 protein concentrations of (i) by applying a statistical modeling technique;
      (iii) calculating a first Youden index for each point of the first ROC curve corresponding to a concentration of CHI3L1 between 6 ng and 7 ng/mL and calculating a second Youden index for each point of the second ROC curve corresponding to a Chit-1 concentration between 275 ng/ml and 285 ng/ml; and
      (iv) identifying a first highest calculated Youden index from the first Youden index from (iii) and a second highest calculated Youden index from the second Youden index from (iii), wherein the first highest calculated Youden index represents the CHI3L1 optimal cutoff concentration and the second highest calculated Youden index represents the Chit-1 optimal cutoff concentration;
   b) performing an immunoassay to determine a concentration of the CHI3L1 protein and a concentration of the Chit-1 protein in a CSF sample obtained from the subject;
   c) comparing the concentration of the CHI3L1 protein in the CSF sample to the CHI3L1 optimal cutoff concentration determined in step (a) and comparing the concentration of the Chit-1 protein in the CSF sample to the Chit-1 optimal cutoff concentration determined in step (a);
   d) categorizing the subject as having ALS if the concentration of the CHI3L1 protein in the CSF sample is equal to or higher than the CHI3L1 optimal cutoff concentration and if the concentration of the Chit-1 protein in the CSF sample is equal to or higher than the Chit-1 optimal cutoff concentration, wherein accuracy of categorization of a subject as having ALS is improved by comparing in combination the concentration of the CHI3L1 protein to the CHI3L1 optimal cutoff concentration and comparing the concentration of the Chit-1 protein to the Chit-1 optimal cutoff concentration when compared to categorization of the subject as having ALS by comparing the concentration of the CHI3L1 protein to the CHI3L1 optimal cutoff concentration or comparing the concentration of the Chit-1 protein to the Chit-1 optimal cutoff concentration; and
   e) administering an anti-inflammatory agent to the subject when the concentration of the CHI3L1 protein in the CSF sample is equal to or higher than the CHI3L1 optimal cutoff concentration and the concentration of the Chit-1 protein in the CSF sample is equal to or higher than the Chit-1 optimal cutoff.

2. The method of claim 1, wherein the Chit-1 optimal cutoff concentration further categorizes a subject having ALS as having fast progressing ALS, slow progressing ALS, and healthy subjects.

3. A method of categorizing a human subject for treatment, wherein the subject is suspected of having or is at risk of having amyotrophic lateral sclerosis (ALS), the method comprising:
   a) performing an immunoassay to determine a concentration of the CHI3L1 protein and a concentration of the Chit-1 protein in a sample of cerebrospinal fluid (CSF) obtained from the subject;
   b) comparing the concentration of the CHI3L1 protein in the CSF sample to a CHI3L1 optimal cutoff concentration of 275 ng/ml to 285 ng/ml and comparing the concentration of the Chit-1 protein in the CSF sample to a Chit-1 optimal cutoff concentration of 6 ng/ml to 7 ng/ml;
   c) categorizing the subject as having ALS if the concentration of the CHI3L1 protein in the CSF sample is equal to or higher than the CHI3L1 optimal cutoff concentration and if the concentration of the Chit-1 protein in the CSF sample is equal to or higher than the Chit-1 optimal cutoff concentration; and
   d) administering an anti-inflammatory agent to the subject when the concentration of the CHI3L1 protein in the CSF sample is equal to or higher than the CHI3L1 optimal cutoff concentration and the concentration of the Chit-1 protein in the CSF sample is equal to or higher than the Chit-1 optimal cutoff.

* * * * *